United States Patent
Guan et al.

(10) Patent No.: US 10,519,148 B2
(45) Date of Patent: Dec. 31, 2019

(54) ACRYLIC ACID DERIVATIVE, PREPARATION METHOD AND USE IN MEDICINE THEREOF

(71) Applicant: Zhejiang Hisun Pharmaceutical Co., Ltd., Taizhou (CN)

(72) Inventors: Dongliang Guan, Taizhou (CN); Shouyi Sheng, Taizhou (CN); Hua Bai, Taizhou (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 0 days.

(21) Appl. No.: 15/766,692

(22) PCT Filed: Oct. 11, 2016

(86) PCT No.: PCT/CN2016/101768
§ 371 (c)(1),
(2) Date: Apr. 6, 2018

(87) PCT Pub. No.: WO2017/080338
PCT Pub. Date: May 18, 2017

(65) Prior Publication Data
US 2018/0291019 A1 Oct. 11, 2018

(30) Foreign Application Priority Data

Nov. 12, 2015 (CN) .......................... 2015 1 0771111

(51) Int. Cl.
C07D 471/04 (2006.01)
A61K 31/437 (2006.01)
A61P 35/00 (2006.01)

(52) U.S. Cl.
CPC .......... *C07D 471/04* (2013.01); *A61K 31/437* (2013.01); *A61P 35/00* (2018.01)

(58) Field of Classification Search
CPC .................................................. C07D 471/04
See application file for complete search history.

(56) References Cited

FOREIGN PATENT DOCUMENTS

| WO | 2011156518 A2 | 12/2011 |
| WO | 2012037410 A2 | 3/2012 |
| WO | 2014191726 A1 | 12/2014 |
| WO | 2015082990 A1 | 6/2015 |
| WO | WO2017136688 | * 8/2017 |

OTHER PUBLICATIONS

Internation Search Report from PCT/CN2016/101768 dated Jan. 11, 2017, pp. 1-3.
Li et al, Endocrine-Therapy-Resistant ESR1 Variants Revealed by Genomic Characterization of Breast-Cancer-Derived Xenografts, vol. 4(6), 28 pages, Sep. 26, 2013.
Patani, George A., et al, Bioisosterism: A Rational Approach in Drug Design, dated May 15, 1996, vol. 96, pp. 3147-3176.
Search Report for Taiwan Application No. 105134387 dated Nov. 12, 2015.
Weiyi Toy, et al, ESR1 ligand binding domain mutations in hormone-resistant breast cancer, Dec. 2013, vol. 45(12), pp. 1439-1445.
De Savi et al., Optimization of a Novel Binding Motif, Journal of Medicinal Chemistry, Oct. 22, 2015, pp. 8128-8140, vol. 58, No. 20.
Japanese Office Action for Application No. 2018-524291 dated Feb. 14, 2019.

* cited by examiner

*Primary Examiner* — Brian E McDowell
(74) *Attorney, Agent, or Firm* — Lerner, David, Littenberg, Krumholz & Mentlik, LLP

(57) ABSTRACT

The present invention relates to an acrylic acid derivative as shown in general formula (I), a stereoisomer, tautomer or pharmaceutically acceptable salt thereof, the preparation method thereof, a pharmaceutical composition containing same, and the use thereof as therapeutic agents, in particular as selective estrogen receptor degraders (SERD), wherein the substituents of general formula (I) are the same as those defined in the description.

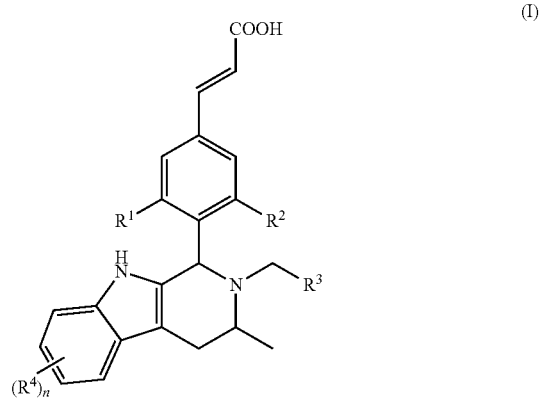

(I)

29 Claims, 4 Drawing Sheets

ACRYLIC ACID DERIVATIVE, PREPARATION METHOD AND USE IN MEDICINE THEREOF

CROSS REFERENCE TO RELATED APPLICATIONS

The present application is a national phase entry under 35 U.S.C. § 371 of International Application No. PCT/CN2016/101768, filed Oct. 11, 2016, which claims priority from Chinese Patent Application No. 201510771111.7 filed Nov. 12, 2015, all of which are hereby incorporated herein by reference.

FIELD OF THE INVENTION

The present invention relates to the field of medicine and, in particular, to a novel acrylic derivative, a stereoisomer, tautomer or pharmaceutically acceptable salt thereof, processes for their preparation, pharmaceutical compositions containing them, and their use as a therapeutic agent, in particular as an estrogen receptor antagonist or an estrogen receptor α downregulator.

BACKGROUND OF THE INVENTION

Estrogen receptor (ER) is a ligand-activated transcriptional regulatory protein that mediates the induction of a variety of biological effects through the interaction with endogenous estrogens. Endogenous estrogens include 17β-estradiol and Estrone. ER has two subtypes, estrogen receptor α (ERα, ESR1 and NR3A) and estrogen receptor β (ERβ, ESR2 and NR3b). Estrogen receptor α and estrogen receptor β are members of the steroid hormone receptor, which is a member of the nuclear receptor family. Similar to the mechanism of the nuclear receptor, ERα is composed of six functional domains (named A to F), which is a ligand-activated transcription factor. After binding to a specific ligand including endogenous estrogens 1713 Estradiol (E2), ERα binds to a genomic sequence into a complex, that is, an estrogen receptor responsive element and a co-regulatory factor bind together to regulate the transcription of the target gene. The ERα gene is located at 6q25.1, encoding the 595A protein, resulting in different subtypes depending on the cleavage sites and the transcription initiation points. In addition to the DNA binding domain (domain C) and the ligand binding domain (E domain), the receptor also includes the N-terminal (A/B domain), the hinge region (D domain which connects the C and E domains) and the C-terminal (F domain). The ERα and ERβ are consistent in C and E domains and have a low consistency in A/B, D and F domains. Both receptors are related to the regulation and growth of the female genital tract and play an important role in the central nervous system, cardiovascular system and bone metabolism. The binding of estrogen and receptor can lead to a variety of cell changes, the regulatory mechanism thereof can be divided into two ways: genome and non-genomic pathways. ER-mediated genomic pathway includes estrogen receptor dimer formation, binding to ERE in the estrogen-regulated gene promoter, mediating aggregation of other regulatory proteins into the promoter, and ultimately leads to an increase or decrease in the mRNA level of the gene. In Estrogen-mediated non-genomic pathway, estrogen reacts with estrogen-binding proteins that are present in or adjacent to the cell membrane of ERs, and even the cell membrane without ERs. The cell responses caused by estrogen through non-genomic pathway, can increase intracellular calcium and NO levels, as well as a variety of intracellular kinase activation, including MAPK, PI3K, PKA and PKC, causing nER phosphorylation and activation.

About 70% of patients who suffer from breast cancer express ER and/or progesterone receptors, indicating that the growth of this tumor cells is hormone-dependent, and the growth of other tumors such as ovarian cancer and endometrial cancer is also dependent on ERα. The treatment of these diseases can be done by inhibiting ER signaling through a variety of ways, including antagonism the binding of ligand to ER, antagonism or down-regulation of ERα, blocking estrogen synthesis, and the like. At the same time the ERα and ERβ are expressed in the endocrine tumors such as adrenal cortical tumors, pancreatic cancer, prostate cancer and thyroid cancer, gastrointestinal system tumors such as colon cancer, esophageal cancer, liver cancer and pancreatic cancer, and lung cancer. Although the above-mentioned treatment has played a role in ER-positive cancer patients, it also leads to drug resistance. Recently, it has been reported that ESR1 mutations may be one of the causes of resistance to metastatic ER-positive breast cancer patients (Toy et al., Nat. Genetic 2013, 45:1439-1445; Li, S. et al Cell Rep. 4, 1116-1130 (2013)). However, in the possible resistance mechanisms, the growth of tumor shows ER dependent activity, and therefore the mechanism by which ERα is selectively reduced provides a better way to block ERα activity mediated early, metastatic and drug resistant cancers.

It has been disclosed that a number of drugs that can be used as selective estrogen receptor downregulator (degrader) (SERD) by now, including GDC-0810 and GDC-0927 from Genentech in clinical phase II and Clinical phase I respectively; AZD-9496 from AstraZeneca in clinical phase I, and a series of SERD patent applications, including WO2011156518, WO2012037410, WO2015082990 and the like. However, there is still a need to study and develop new estrogen receptor α downregulators.

SUMMARY OF THE INVENTION

It is an object of the present invention to provide an acrylic derivative having an estrogen receptor antagonistic activity whose structure is different from that in the prior art.

Thus, according to a first aspect of the present invention, the present invention provides a compound represented by general formula (I), or a stereoisomer, tautomer or pharmaceutically acceptable salt thereof:

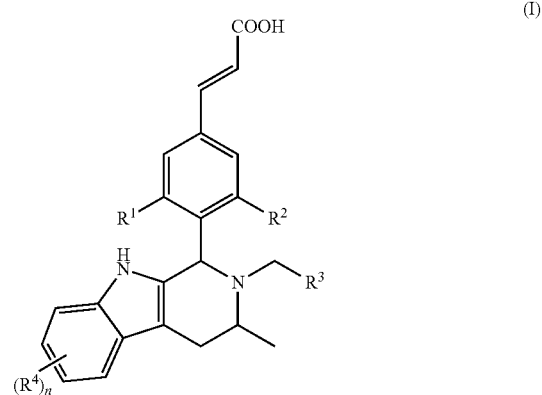

wherein:

R¹ and R² are each independently selected from hydrogen atom or halogen, wherein said halogen is preferably F;

R³ is selected from following groups:

(i) cycloalkyl, heterocyclyl, aryl or heteroaryl, wherein said cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —NR⁵R⁶, —C(O)NR⁵R⁶, —C(O)R⁷, —SO₂R⁷, —C(O)OR⁷ or —NR⁵C(O)R⁶;

(ii) alkyl, wherein said alkyl is further substituted by one or more groups selected from hydroxy, nitro, cyano, alkoxy, cycloalkyl, heterocyclyl, aryl, heteroaryl, —NR⁵R⁶, —C(O)NR⁵R⁶, —C(O)R⁷, —SO₂R⁷, —C(O)OR⁷ or —NR⁵C(O)R⁶, wherein said alkoxy, cycloalkyl, heterocyclyl, aryl or heteroaryl is optionally further substituted by one or more groups selected from halogen, hydroxy, nitro, cyano, alkoxy, —C(O)NR⁵R⁶, —C(O)R⁷, —SO₂R⁷, —C(O)OR⁷ or —NR⁵C(O)R⁶, wherein said halogen is preferably F;

R⁴ are each independently selected from hydrogen atom, halogen, alkyl, alkoxy, trifluoromethyl, cyano, —C(O)NR⁵R⁶, —C(O)R⁷, —SO₂R⁷, —C(O)OR⁷ or —NR⁵C(O)R⁶, wherein said alkyl or alkoxy is optionally further substituted by one or more groups selected from halogen, —C(O)NR⁵R⁶, —C(O)R⁷, —SO₂R⁷, —C(O)OR⁷ or —NR⁵C(O)R⁶;

R⁵ is selected from hydrogen atom or alkyl;

R⁶ is selected from hydrogen atom, alkyl, cycloalkyl, aryl or heteroaryl, wherein said alkyl, cycloalkyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —NR⁸R⁹, —C(O)NR⁸R⁹, —C(O)R¹⁰, —SO₂R¹⁰, —C(O)OR¹⁰ or —NR⁸C(O)R⁹;

or, R⁵ and R⁶ together with the atoms attached to them form a 4- to 8-membered heterocyclyl, wherein said heterocyclyl is optionally further substituted by one or more groups selected from alkyl, halogen, hydroxy, cyano, nitro, cycloalkyl, heterocyclyl, aryl, heteroaryl, —NR⁸R⁹, —C(O)NR⁸R⁹, —C(O)R¹⁰, —SO₂R¹⁰, —C(O)OR¹⁰ or —NR⁸C(O)R⁹; R⁷ is selected from hydrogen atom, alkyl, cycloalkyl, heterocyclyl, aryl or heteroaryl, wherein said alkyl, cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —NR⁸R⁹, —C(O)NR⁸R⁹, —C(O)R¹⁰, —SO₂R¹⁰, —C(O)OR¹⁰ or —NR⁸C(O)R⁹;

R⁸, R⁹ and R¹⁰ are each independently selected from hydrogen atom, alkyl, cycloalkyl, heterocyclyl, aryl or heteroaryl, wherein said alkyl, cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, carboxy or carboxylate group; and n is 0, 1, 2, 3 or 4.

In another embodiment of the present invention, the compound of general formula (I), or the stereoisomer, tautomer or pharmaceutically acceptable salt thereof, is a compound of general formula (II), a stereoisomer, tautomer or pharmaceutically acceptable salt thereof:

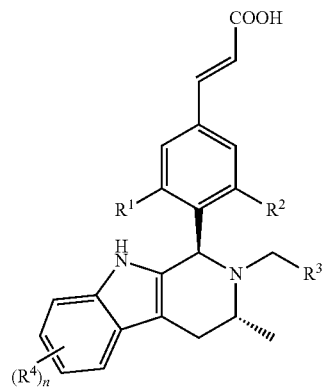

wherein, R¹, R², R³, R⁴ and n are defined as in general formula (I).

In a preferred embodiment of the present invention, the compounds of general formula (I) or (II), or the stereoisomer, tautomer or pharmaceutically acceptable salt thereof, wherein:

said alkyl is preferably $C_1$-$C_{10}$ alkyl;
said alkoxy is preferably $C_1$-$C_{10}$ alkoxy;
said—cycloalkyl is preferably $C_3$-$C_{12}$ cycloalkyl;
said heterocyclyl is preferably $C_3$-$C_{10}$ heterocyclyl;
said aryl is preferably $C_6$-$C_{10}$ aryl;
said heteroaryl is preferably 5- to 10-membered heteroaryl.

In a preferred embodiment of the present invention, the compounds of general formula (I) or (II), or the stereoisomer, tautomer or pharmaceutically acceptable salt thereof, wherein R⁴ are each independently selected from hydrogen atom, $C_1$-$C_3$ alkyl, halogen, alkoxy, trifluoromethyl or cyano.

In one embodiment of the present invention, the compounds of general formula (I) or (II), or the stereoisomer, tautomer or pharmaceutically acceptable salt thereof, wherein R³ is cyclopropyl, wherein said cyclopropyl is optionally further substituted by one or more groups selected from hydroxy, halogen, haloalkyl, nitro, cyano, alkyl, alkoxy, cycloalkyl, heterocyclyl, aryl, heteroaryl, —NR⁵R⁶, —C(O)NR⁵R⁶, —C(O)R, —SO₂R⁷, —C(O)OR⁷ or —NR⁵C(O)R⁶, wherein said cyclopropyl is preferably substituted by halogen, more preferably substituted by F; and R⁵, R⁶ and R⁷ are defined as in general formula (I).

In one embodiment of the present invention, the compounds of general formula (I) or (II), or the stereoisomer, tautomer or pharmaceutically acceptable salt thereof, wherein R³ is selected from cyclopentyl or cyclohexyl, wherein said cyclopentyl or cyclohexyl is optionally further substituted by one or more groups selected from hydroxy, halogen, haloalkyl, nitro, cyano, alkyl, alkoxy, cycloalkyl, heterocyclyl, aryl, heteroaryl, —NR⁵R⁶, —C(O)NR⁵R⁶, —C(O)R⁷, —SO₂R⁷, —C(O)OR⁷ or —NR⁵C(O)R⁶, wherein said cyclopentyl or cyclohexyl is preferably substituted by halogen, more preferably substituted by F; and R⁵, R⁶ and R⁷ are defined as in general formula (I).

In one embodiment of the present invention, the compounds of general formula (I) or (II), or the stereoisomer, tautomer or pharmaceutically acceptable salt thereof, wherein R³ is alkyl, wherein said alkyl is further substituted by one or more groups selected from hydroxy, nitro, cyano, alkoxy, cycloalkyl, heterocyclyl, aryl, heteroaryl, —NR⁵R⁶, —C(O)NR⁵R⁶, —C(O)R, —SO₂R⁷, —C(O)OR⁷ or —NR⁵C(O)R⁶, wherein said alkoxy, cycloalkyl, heterocyclyl, aryl or heteroaryl is optionally further substituted by one or more F; and R⁵, R⁶ and R⁷ are defined as in general formula (I).

In one embodiment of the present invention, the compounds of general formula (I) or (II), or the stereoisomer, tautomer or pharmaceutically acceptable salt thereof, wherein:

$R^1$ and $R^2$ are each independently selected from halogen, wherein said halogen is preferably F;

$R^3$ is selected from the following groups consisting of:

(i) cyclopropyl, cyclopentyl, cyclohexyl, $C_3$-$C_{10}$ heterocyclyl, $C_6$-$C_{10}$ aryl or 5- to 10-membered heteroaryl, wherein said cyclopropyl, cyclopentyl, cyclohexyl, $C_3$-$C_{10}$ heterocyclyl, $C_6$-$C_{10}$ aryl or 5- to 10-membered heteroaryl is optionally further substituted by one or more halogen, wherein said halogen is preferably F;

(ii) $C_1$-$C_{10}$ alkyl, wherein said alkyl is further substituted by one or more hydroxy;

$R^4$ is hydrogen atom.

In one embodiment of the present invention, the compounds of general formula (I) or (II), or the stereoisomer, tautomer or pharmaceutically acceptable salt thereof, wherein:

$R^1$ and $R^2$ are each independently selected from halogen, preferably F;

$R^3$ is selected from cyclopropyl, cyclopentyl, cyclohexyl, $C_3$-$C_{10}$ heterocyclyl, $C_6$-$C_{10}$ aryl or 5- to 10-membered heteroaryl, wherein said cyclopropyl, cyclopentyl, cyclohexyl, $C_3$-$C_{10}$ heterocyclyl, $C_6$-$C_{10}$ aryl or 5- to 10-membered heteroaryl is optionally further substituted by one or more halogen, wherein said halogen is preferably F, Cl or Br, more preferably F;

$R^4$ are each independently selected from $C_1$-$C_6$ alkyl or halogen, wherein said halogen is preferably F, Cl or Br, more preferably F.

In one embodiment of the present invention, the compounds of general formula (I) or (II), or the stereoisomer, tautomer or pharmaceutically acceptable salt thereof, wherein:

$R^1$ and $R^2$ are each independently selected from halogen, preferably F;

$R^3$ is selected from cyclopropyl, wherein said cyclopropyl is further substituted by one or more halogen, wherein said halogen is preferably F;

$R^4$ are each independently selected from $C_1$-$C_6$ alkyl or halogen, preferably F.

In one embodiment of the present invention, the compounds of general formula (I) or (II), or the stereoisomer, tautomer or pharmaceutically acceptable salt thereof, wherein:

$R^1$ and $R^2$ are each independently selected from halogen, preferably F;

$R^3$ is

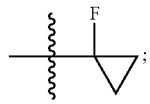 [SMILES: *C1(F)CC1]

$R^4$ is F.

Typical compounds of the invention include, but are not limited to, the compounds described in Table 1, or a stereoisomer, tautomer or pharmaceutically acceptable salt thereof:

TABLE 1

Structures and nomenclatures of compounds of Examples 1-13

| No. of Examples | Structure | nomenclature |
|---|---|---|
| 1 | 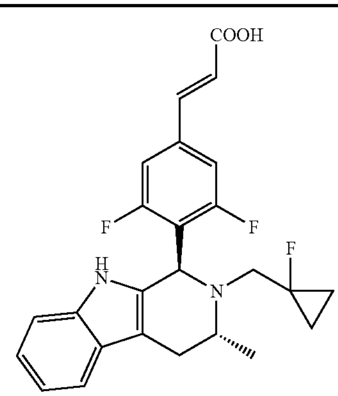 | (E)-3-(3,5-difluoro-4-((1R,3R)-2-((1-fluorocyclopropyl)methyl)-3-methyl-2,3,4,9-tetrahydro-1H-pyrido[3,4-b]indol-1-yl)phenyl)acrylic acid |

TABLE 1-continued

Structures and nomenclatures of compounds of Examples 1-13

| No. of Examples | Structure | nomenclature |
|---|---|---|
| 2 | 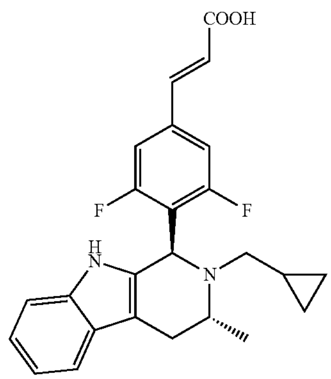 [SMILES: C[C@@H]1Cc2c([nH]c3ccccc23)[C@@H](c2c(F)cc(/C=C/C(=O)O)cc2F)N1CC1CC1] | (E)-3-(4-((1R,3R)-2-(cyclopropylmethyl)-3-methyl-2,3,4,9-tetrahydro-1H-pyrido[3,4-b]indol-1-yl)-3,5-difluorophenyl)acrylic acid |
| 3 | 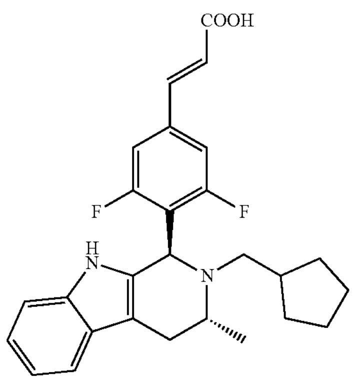 [SMILES: C[C@@H]1Cc2c([nH]c3ccccc23)[C@@H](c2c(F)cc(/C=C/C(=O)O)cc2F)N1CC1CCCC1] | (E)-3-(4-((1R,3R)-2-(cyclopentylmethyl)-3-methyl-2,3,4,9-tetrahydro-1H-pyrido[3,4-b]indol-1-yl)-3,5-difluorophenyl)acrylic acid |
| 4 | 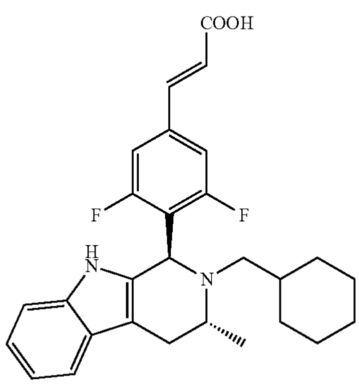 [SMILES: C[C@@H]1Cc2c([nH]c3ccccc23)[C@@H](c2c(F)cc(/C=C/C(=O)O)cc2F)N1CC1CCCCC1] | (E)-3-(4-((1R,3R)-2-(cyclohexylmethyl)-3-methyl-2,3,4,9-tetrahydro-1H-pyrido[3,4-b]indol-1-yl)-3,5-difluorophenyl)acrylic acid |
| 5 | 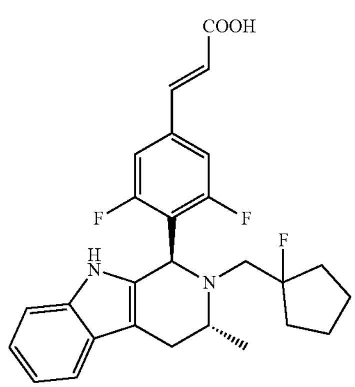 [SMILES: C[C@@H]1Cc2c([nH]c3ccccc23)[C@@H](c2c(F)cc(/C=C/C(=O)O)cc2F)N1CC1(F)CCCC1] | (E)-3-(3,5-difluoro-4-((1R,3R)-2-((1-fluorocyclopentyl)methyl)-3-methyl-2,3,4,9-tetrahydro-1H-pyrido[3,4-b]indol-1-yl)phenyl)acrylic acid |

TABLE 1-continued

Structures and nomenclatures of compounds of Examples 1-13

| No. of Examples | Structure | nomenclature |
|---|---|---|
| 6 | 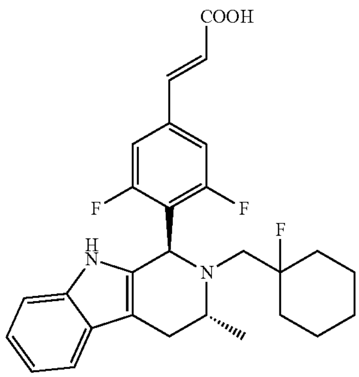 [SMILES: C[C@@H]1Cc2c([nH]c3ccccc23)[C@@H](c2c(F)cc(/C=C/C(=O)O)cc2F)N1CC1(F)CCCCC1] | (E)-3-(3,5-difluoro-4-((1R,3R)-2-((1-fluorocyclohexyl)methyl)-3-methyl-2,3,4,9-tetrahydro-1H-pyrido[3,4-b]indol-1-yl)phenyl)acrylic acid |
| 7 | 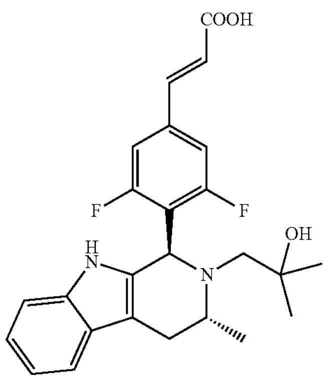 [SMILES: C[C@@H]1Cc2c([nH]c3ccccc23)[C@@H](c2c(F)cc(/C=C/C(=O)O)cc2F)N1CC(C)(C)O] | (E)-3-(3,5-difluoro-4-((1R,3R)-2-(2-hydroxy-2-methylpropyl)-3-methyl-2,3,4,9-tetrahydro-1H-pyrido[3,4-b]indol-1-yl)phenyl)acrylic acid |
| 8 | 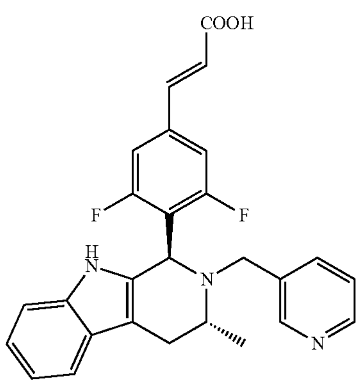 [SMILES: C[C@@H]1Cc2c([nH]c3ccccc23)[C@@H](c2c(F)cc(/C=C/C(=O)O)cc2F)N1Cc1cccnc1] | (E)-3-(3,5-difluoro-4-((1R,3R)-3-methyl-2-(pyridin-3-ylmethyl)-2,3,4,9-tetrahydro-1H-pyrido[3,4-b]indol-1-yl)phenyl)acrylic acid |
| 9 | 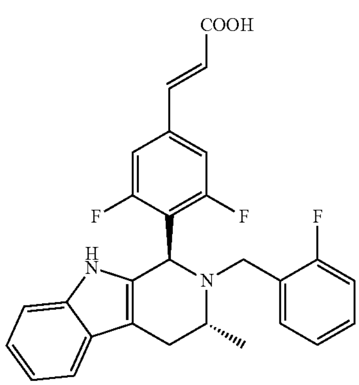 [SMILES: C[C@@H]1Cc2c([nH]c3ccccc23)[C@@H](c2c(F)cc(/C=C/C(=O)O)cc2F)N1Cc1ccccc1F] | (E)-3-(3,5-difluoro-4-((1R,3R)-2-(2-fluorobenzyl)-3-methyl-2,3,4,9-tetrahydro-1H-pyrido[3,4-b]indol-1-yl)phenyl)acrylic acid |

TABLE 1-continued

Structures and nomenclatures of compounds of Examples 1-13

| No. of Examples | Structure | nomenclature |
|---|---|---|
| 10 | 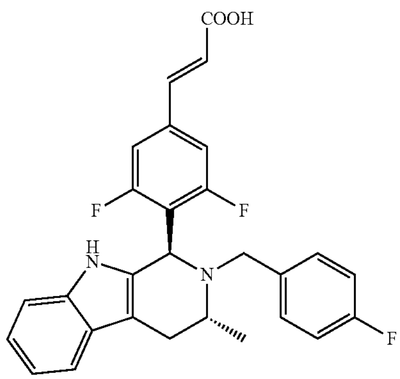 [SMILES: C[C@@H]1Cc2c([nH]c3ccccc23)[C@@H](c2c(F)cc(/C=C/C(=O)O)cc2F)N1Cc1ccc(F)cc1] | (E)-3-(3,5-difluoro-4-((1R,3R)-2-(4-fluorobenzyl)-3-methyl-2,3,4,9-tetrahydro-1H-pyrido[3,4-b]indol-1-yl)phenyl)acrylic acid |
| 11 | 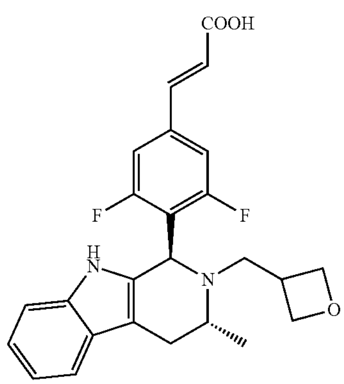 [SMILES: C[C@@H]1Cc2c([nH]c3ccccc23)[C@@H](c2c(F)cc(/C=C/C(=O)O)cc2F)N1CC1COC1] | (E)-3-(3,5-difluoro-4-((1R,3R)-3-methyl-2-(oxetane-3-ylmethyl)-2,3,4,9-tetrahydro-1H-pyrido[3,4-b]indol-1-yl)phenyl)acrylic acid |
| 12 | 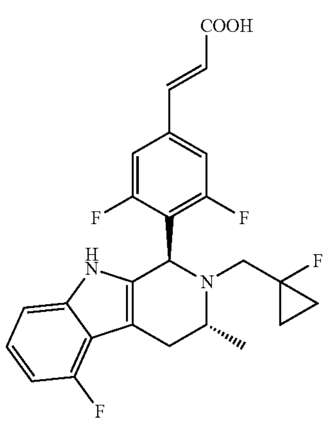 [SMILES: C[C@@H]1Cc2c([nH]c3cccc(F)c23)[C@@H](c2c(F)cc(/C=C/C(=O)O)cc2F)N1CC1(F)CC1] | (E)-3-(3,5-difluoro-4-((1R,3R)-5-fluoro-2-(1-fluorocyclopropyl)methyl)-3-methyl-2,3,4,9-tetrahydro-1H-pyrido[3,4-b]indol-1-yl)phenyl)acrylic acid |

TABLE 1-continued

Structures and nomenclatures of compounds of Examples 1-13

| No. of Examples | Structure | nomenclature |
|---|---|---|
| 13 | 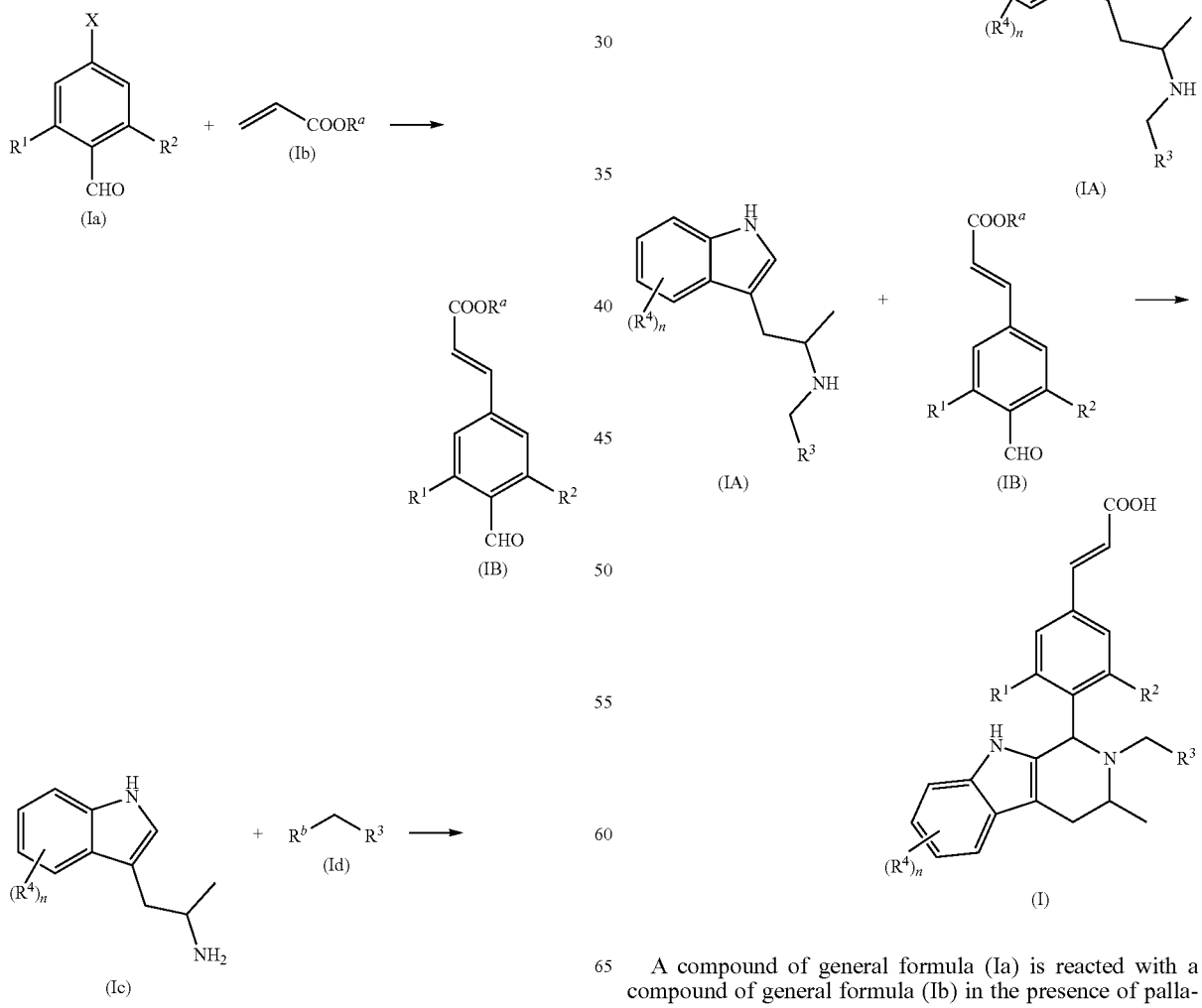 | (E)-3-(3,5-difluoro-4-((1S,3S)-5-fluoro-2-(1-fluorocyclopropyl)methyl)-3-methyl-2,3,4,9-tetrahydro-1H-pyrido[3,4-b]indol-1-yl)phenyl)acrylic acid |

Another aspect of the present invention provides a process for the preparation of the compound of general formula (I) or the salt thereof, comprising the following steps:

A compound of general formula (Ia) is reacted with a compound of general formula (Ib) in the presence of palladium acetate and tri-o-tolylphosphine under basic condition to obtain a compound of general formula (IB); a compound of general formula (Ic) is reacted with a compound of general formula (Id) under basic condition to obtain a compound of general formula (IA); and the compound of general formula (IA) is reacted with the compound of general formula (IB) under acidic condition and further ester hydrolysis to obtain the compound of general formula (I);

wherein: X is halogen, preferably Br; $R^a$ is alkyl; $R^b$ is a leaving group, preferably halogen and sulfonate ester, more preferably Br or mesylate ester; $R^1$ to $R^4$ and n are defined as in general formula (I).

Another aspect of the present invention provides a process for the preparation of the compound of general formula (II) or the salt thereof, comprising the following steps:

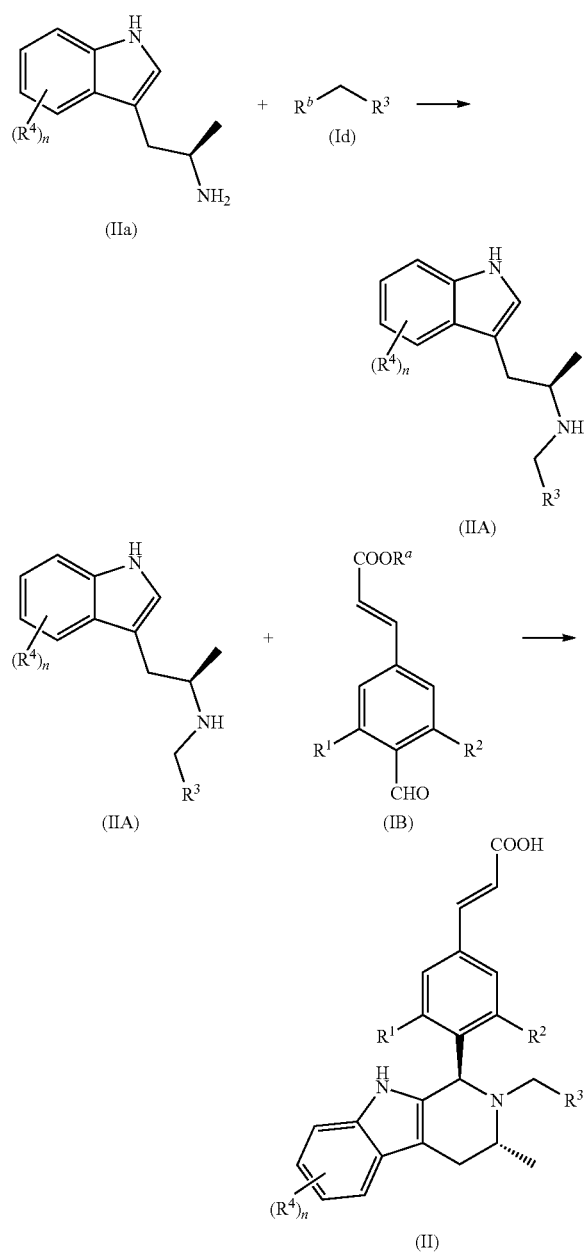

A compound of general formula (IIa) is reacted with a compound of general formula (Id) under basic condition to obtain a compound of general formula (IIA); and the compound of general formula (IIA) is reacted with a compound of general formula (IB) under acidic condition and further ester hydrolysis to obtain the compound of general formula (II);

wherein: $R^a$ is alkyl; $R^b$ is a leaving group, preferably halogen and sulfonate ester, more preferably Br or mesylate ester; $R^1$, $R^2$, $R^3$ and $R^4$ and n are defined as in general formula (I).

In the above preparation process, the reagent for providing an acidic condition is an inorganic acid or an organic acid, and the inorganic acid is preferably selected from hydrochloric acid, sulfuric acid, phosphoric acid, more preferably hydrochloric acid; the organic acid is preferably selected from formic acid, acetic acid, more preferably acetic acid.

In the above preparation process, the reagent for providing an basic condition is an organic base or an inorganic base, and the organic base is preferably selected from the group consisting of diisopropylethylamine, diisopropylamine, pyridine, triethylamine, piperidine, N-methylpiperazine, 4-dimethylaminopyridine, more preferably diisopropylamine and triethylamine; the inorganic base is preferably selected from the group consisting of sodium carbonate, potassium carbonate, cesium carbonate, sodium hydroxide, potassium hydroxide, more preferably sodium carbonate and sodium hydroxide.

Further, the present invention provides a pharmaceutical composition comprising an effective amount of the compound of general formula (I) or (II) or the stereoisomer, tautomer or pharmaceutically acceptable salt thereof, and a pharmaceutically acceptable carrier, an excipient, or a combination thereof. The composition optionally further comprises an antioxidant or a metal chelating agent.

The present invention also provides a method for selectively down-regulating estrogen receptors which comprises reacting the compound of general formula (I) or (II) or the stereoisomer, tautomer or pharmaceutically acceptable salt thereof, or the pharmaceutical composition thereof in contact with estrogen receptor, wherein the estrogen receptor is preferably estrogen receptor α.

The present invention also provides use of the compound of general formula (I) or (II) or the stereoisomer thereof, tautomer or pharmaceutically acceptable salt thereof, or the pharmaceutical composition thereof, in the preparation of a medicament for the treatment of estrogen receptor-mediated diseases, wherein the diseases are preferably cancers, wherein the cancers are preferably breast cancer and gynecological cancers, wherein the gynecological cancers are preferably ovarian cancer and endometrial cancer, wherein the estrogen receptor is preferably estrogen receptor α.

The present invention also provides use of the compound of general formula (I) or (II) or the stereoisomer, tautomer or pharmaceutically acceptable salt thereof, or the pharmaceutical composition thereof, in the preparation of a selective estrogen receptor downregulator, preferably an estrogen receptor α downregulator.

The present invention also provides the compound of general formula (I) or (II) or the stereoisomer, tautomer or pharmaceutically acceptable salt thereof, or a pharmaceutical composition thereof, in combination with one or more other suitable antitumor agents for the treatment of estrogen receptor mediated diseases, wherein the diseases are preferably cancers, wherein the cancers are preferably breast cancer or gynecological cancers, wherein said gynecological cancers are preferably ovarian cancer or endometrial cancer, wherein said estrogen receptor is preferably estrogen receptor α, wherein said other antitumor drugs comprises alkylating agents, antimetabolite agents, natural products having antitumor activity and derivatives thereof, cytotoxic agents or agents blocking immune cell migration.

Suitable other antitumor drugs include alkylating agents (but not limited to nitrogen mustard, ethylenimine derivative, alkyl sulfonate ester, nitrosourea and triazene), such as uramustine, nitrogen mustard, cyclophosphamide, ifosfamide, melphalan, chlorambucil, pipobroman, thiotepa, busulfan, carmustine, lomustine, streptozocin, dacarbazine, and temozolomide.

Suitable other antitumor drugs also include, for example, antimetabolites (including but not limited to folate antagonists, pyrimidine analogs, purine analogs, and adenosine deaminase inhibitors), such as methotrexate, 5-fluorouracil, fluorouracil, cytarabine, 6-mercaptopurine, 6-thiouracil, fludarabine phosphate, pentostatin and gemcitabine.

Suitable other antitumor drugs also include, for example, certain natural products with antitumor activity and their derivatives (e.g., vinca alkaloids, antitumor antibiotics, enzymes, lymphokines, etc.), such as vinblastine, vincristine, Vindesine, Bleomycin, actinomycin D, daunorubicin, doxorubicin, epirubicin, idarubicin, cytarabine, paclitaxel, plicamycin, deoxycoformycin, mitomycin-C, L-asparaginase, interferon (especially IFN-α), etoposide and teniposide.

Suitable other antitumor drugs also include cytotoxic drugs including Navelbine, CPT-11, anastrozole, letrozole, capecitabine and droloxifene, topoisomerase inhibitor, procarbazine, mitoxantrone, platinum ligand complex such as cisplatin and carboplatin; biological response modulators; growth inhibitors; anti-hormonal therapeutic drugs; folinic acid; tegafur and hematopoietic growth factors are also applicable.

In addition, suitable other antitumor drugs also include antibodies therapeutic drugs such as trastuzumab, co-stimulatory molecule antibodies such as CTLA-4, 4-1BB and PD-1 or cytokine antibodies (IL-10, IGF-β etc.); drugs that block immune cell migration, such as chemokine receptor antagonists, including CCR2 and CCR4; also include drugs that enhance the immune system, such as adjuvant or adoptive T cell transfer; anticancer vaccines, including dendritic cells synthetic peptides, DNA vaccines and recombinant viruses.

Methods of safe and effective administration of most chemotherapeutic drugs (antitumor drugs) known to those skilled in the art, as well as their administration criteria, have been discussed in the standard literature, such as "physicians desk reference" (PDR, e.g. 1996 edition, medical Economics Company, Montvale, N.J.) discloses the administration method of many chemotherapeutic drugs, the disclosure of which is incorporated herein by reference.

Unless otherwise indicated, certain terms used in the specification and claims are defined as follows:

As a group or a part of a group, "alkyl" refers to an aliphatic hydrocarbon group comprising a $C_1$-$C_{20}$ linear or branched chain, preferably $C_1$-$C_{10}$ alkyl, more preferably $C_1$-$C_6$ alkyl, most preferably $C_1$-$C_3$ alkyl. Examples of alkyl group includes, but not limited to, methyl, ethyl, n-propyl, isopropyl, n-butyl, isobutyl, t-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl may be substituted or unsubstituted.

As a group or a part of a group, "alkynyl" refers to an aliphatic hydrocarbon group containing a carbon-carbon triple bond, which may be straight or branched, preferably $C_2$-$C_{10}$ alkynyl, more preferably $C_2$-$C_6$ alkynyl, most preferably $C_2$-$C_4$ alkynyl. Examples of alkynyl group include, but not limited to, ethynyl, 1-propynyl, 2-propynyl, 1-, 2- or 3-butynyl and so on. The alkynyl may be substituted or unsubstituted.

"Cycloalkyl" refers to a carbon ring of saturated or partially saturated monocyclic, fused, bridged and spiro, including monocyclic cycloalkyl, fused cycloalkyl, bridged cycloalkyl and spiro cycloalkyl, preferably $C_3$-$C_{12}$ cycloalkyl, more preferably $C_3$-$C_8$ cycloalkyl, and most preferably $C_3$-$C_6$ cycloalkyl. Examples of monocyclic cycloalkyl groups include, but not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl and the like, preferably cyclopropyl, cyclohexenyl.

"Spiro cycloalkyl" refers to a 5 to 18 membered polycyclic group having two or more ring structures, with a single ring sharing one common carbon atom (named spiro atom), which contains one or more double bonds inside the ring, but none of the rings has a completely conjugated n electron aromatic system. Preferably a spiro cycloalkyl is 6 to 14 membered, more preferably 7 to 10 membered. According to the number of the common spiro atom between the rings, spiro cycloalkyl is divided into mono-spirocyclic ring, di-spirocyclic ring or poly-spirocyclic ring, preferably mono-spirocyclic ring or di-spirocyclic ring. More preferably spiro cycloalkyl is 4-membered/5-membered, 4-membered/6-membered, 5-membered/5-membered, or 5-membered/6-membered. Non-limiting examples of "spiro cycloalkyl" include, but not limited to, spiro[4.5]decyl, spiro[4.4]nonyl, spiro[3.5]nonyl, spiro[2.4]heptyl.

"Fused cycloalkyl" refers to 5 to 18 membered, all-carbon polycyclic groups containing two or more ring structure sharing an adjacent pair of carbon atoms, wherein one or more rings may contain one or more double bonds, but none of the rings has completely conjugated n electron aromatic system. Preferably a fused cycloalkyl is 6 to 12 membered, more preferably 7 to 10 membered. According to the number of membered ring, fused cycloalkyl can be divided into bicyclic ring, tricyclic ring, tetracyclic ring or polycyclic ring fused cycloalkyl, preferably bicyclic ring or tricyclic ring fused cycloalkyl. More preferably fused cycloalkyl is 5-membered/5-membered, or 5-membered/6-membered bicyclic ring fused cycloalkyl. Non-limiting examples of "fused cycloalkyl" include, but not limited to, bicyclo[3.1.0]hexyl, bicyclo[3.2.0]hept-1-enyl, bicyclo[3.2.0]heptyl, decahydronaphthyl or tetradecahydrophenanthryl.

"Bridged cycloalkyl" refers to 5 to 18 membered all-carbon polycyclic groups containing two or more ring structures sharing two carbon atoms which are not connected directly, wherein one or more rings may contain one or more double bonds, but none of the rings has completely conjugated π electron aromatic system. Preferably a bridged cycloalkyl is 6 to 12 membered, more preferably 7 to 10 membered. Preferably a bridged cycloalkyl is 6 to 14 membered, more preferably 7 to 10 membered. According to the number of membered ring, bridged cycloalkyl can be divided into bicyclic ring, tricyclic ring, tetracyclic ring or polycyclic ring bridged cycloalkyl, preferably bicyclic ring, tricyclic ring or tetracyclic ring, more preferably bicyclic ring or tricyclic ring bridged cycloalkyl. Non-limiting examples of "bridged cycloalkyl" include, but not limited to, (1s,4s)-bicyclo[2.2.1]heptyl, bicyclo[3.2.1]octyl, (1s,5s)-bicyclo[3.3.1]nonyl, bicyclo[2.2.2]octyl, (1r,5r)-bicyclo[3.3.2]decyl.

Said cycloalkyl can be fused to the ring of aryl, heteroaryl or heterocyclyl, wherein said ring connected with parent structure is cycloalkyl. Non-limiting examples include, but not limited to, indanyl, tetrahydronaphthyl, benzocycloheptyl and the like. The cycloalkyl group may optionally be substituted or unsubstituted.

"Heterocyclyl", "heterocycle" or "heterocyclic" are used interchangeably herein to refer to a non-aromatic heterocyclyl in which one or more ring-forming atoms are heteroatoms such as oxygen, nitrogen, sulfur atoms and the like, including monocyclic, fused cyclic, bridged cyclic and spiro cyclic, i.e. including monocyclic heterocyclyl, bridged heterocyclyl, fused heterocyclyl and spiro heterocyclyl. Preferably a heterocyclyl is 5 to 7 membered monocyclic or 7 to 10 membered bis- or tricyclic rings which may contain 1, 2 or 3 atoms selected from nitrogen, oxygen and/or sulfur. Examples of "heterocyclyl" include, but not limited to, morpholinyl, thiomorpholinyl, tetrahydropyranyl, 1,1-dioxo-thiomorpholinyl, piperidinyl, 2-oxo-piperidinyl, pyrrolidinyl, 2-oxo-pyrrolidinyl, piperazin-2-one, 8-oxa-3-azabicyclo[3.2.1]octyl and piperazinyl. The heterocyclyl group may be substituted or unsubstituted.

"Spiro heterocyclyl" refers to 5 to 18 membered polyclic groups having two or more ring structures, with a single ring sharing one common carbon atom, wherein the said ring contains one or more double bonds, but none of the rings has a completely conjugated π electron aromatic system, wherein one or more atoms in the ring are selected from heteroatom N, O, or S(O)m (wherein m is selected from 0, 1 or 2), the remaining atoms in the ring are C. Preferably a spiro heterocyclyl group is 6 to 14 membered, more preferably 7 to 10 membered. According to the number of common spiro atom, spiro heterocyclyl is divided into mono-spiro heterocyclyl, di-spiro heterocyclyl or poly-spiro heterocyclyl, preferably mono-spiro heterocyclyl and di-spiro heterocyclyl. More preferably spiro heterocyclyl is 4-membered/4-membered, 4-membered/5-membered, 4-membered/6-membered, 5-membered/5-membered, or 5-membered/6-membered mono-spiro heterocyclyl. Non-limiting examples of spiro heterocyclyl include, but not limited to, 1,7-dioxaspiro[4.5]decyl, 2-oxa-7-azaspiro[4.4]nonyl, 7-oxaspiro[3.5]nonyl and 5-oxaspiro[2.4]heptyl.

"Fused heterocyclyl" refers to all-carbon polycyclic groups containing two or more ring structure sharing an adjacent pair of carbon atoms, wherein one or more rings may contain one or more double bonds, but none of the rings has completely conjugated π electron aromatic system, wherein one or more atoms in the ring are selected from heteroatom N, O, or S(O)m (wherein m is an integer of 0 to 2), the remaining atoms in the ring are C. Preferably a fused heterocyclyl group is 6 to 14 membered, more preferably 7 to 10 membered. According to the number of membered ring, fused heterocyclyl can be divided into bicyclic ring, tricyclic ring, tetracyclic ring or polycyclic ring fused heterocyclyl, preferably bicyclic ring or tricyclic ring, more preferably 5-membered/5-membered or 5-membered/6-membered bicyclic ring fused heterocyclyl. Non-limiting examples of fused heterocyclyl include, but not limited to, octahydro-pyrrolo[3,4-c]pyrrolyl, octahydro-1H-isoindolyl, 3-azabicyclo[3.1.0]hexyl, octahydrobenzo[b][1,4]dioxine.

"Bridged heterocyclyl" refers to 5 to 14 membered, 5 to 18 membered polycyclic groups containing two or more ring structures sharing two carbon atoms which are not connected directly, wherein one or more rings may contain one or more double bonds but none of the rings has completely conjugated π electron aromatic system, wherein one or more atoms in the ring is selected from heteroatoms N, O, or S(O)m (wherein m is an integer of 0 to 2), the remaining atoms in the ring are C. Preferably a bridged heterocyclyl is 6 to 14 membered, more preferably 7 to 10 membered. According to the number of membered ring, bridged heterocyclyl group can be divided into bicyclic ring, tricyclic ring, tetracyclic ring or polycyclic ring bridged heterocyclyl, preferably bicyclic ring, tricyclic ring or tetracyclic ring, more preferably bicyclic ring or tricyclic ring. Non-limiting examples of bridged heterocyclyl include, but not limited to, 2-aza-bicyclo[2.2.1]heptyl, 2-aza-bicyclo[2.2.2]octyl, 2-aza-bicyclo[3.3.2]decyl.

Said ring of heterocyclyl can be fused to the ring of aryl, heteroaryl or heterocyclyl, wherein the ring connected with parent structure is heterocyclyl. The heterocyclyl may optionally be substituted or unsubstituted.

"Aryl" refers to a carbocyclic aromatic system containing one or two rings, wherein the rings may be linked together in a fused manner. The term "aryl" includes aromatic groups such as phenyl, naphthyl, tetrahydronaphthyl. Preferably the aryl group is $C_6$-$C_{10}$ aryl, more preferably the aryl is phenyl and naphthyl, most preferably phenyl. The aryl may be substituted or unsubstituted. The "aryl" may be fused to heteroaryl, heterocyclyl or cycloalkyl, wherein the ring connected with parent structure is aryl ring. Non-limiting examples include, but not limited to,

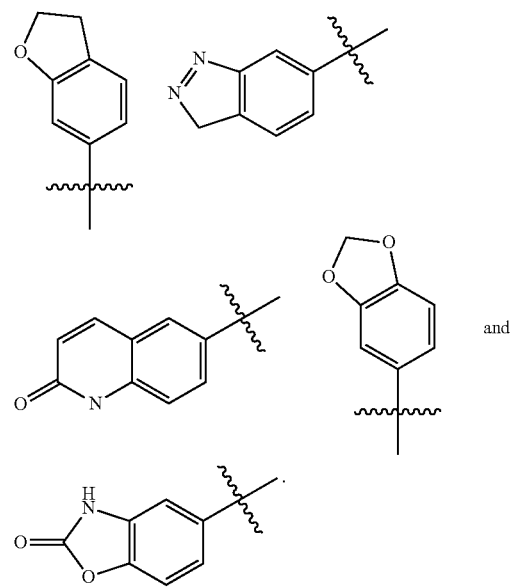

and

"Heteroaryl" refers to an aromatic 5- to 6-membered monocyclic ring or 9 to 10-membered bicyclic ring which may contain 1 to 4 atoms selected from nitrogen, oxygen and/or sulfur. Examples of "heteroaryl" include, but not limited to, furyl, pyridyl, 2-oxo-1,2-dihydropyridyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzodioxolyl, benzimidazolyl, indolyl, isoindolyl, 1,3-dioxo-isoindolyl, quinolinyl, indazolyl, benzoisothiazolyl, benzoxazolyl and benzoisoxazolyl. The heteroaryl group may be substituted or unsubstituted. The heteroaryl ring may be fused to an aryl, heterocyclyl or cycloalkyl ring, wherein the ring connected with parent structure is heteroaryl ring. Non-limiting examples include, but not limited to,

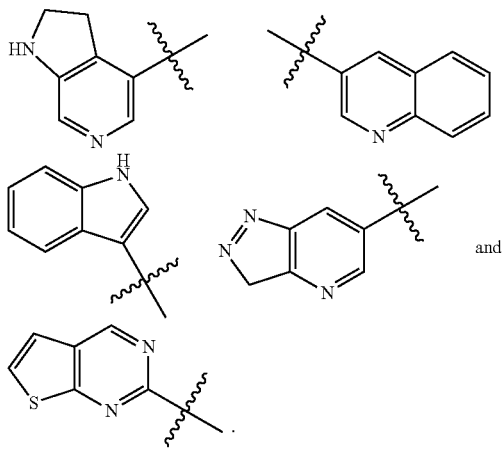

"Alkoxy" refers to an (alkyl-O—) group. Wherein, alkyl is defined as herein. $C_1$-$C_6$ alkoxy is preferred. Examples thereof include, but not limited to, methoxy, ethoxy, n-propoxy, isopropoxy, n-butoxy, isobutoxy, tert-butoxy and the like.

"Hydroxy" refers to an —OH group.

"Halogen" refers to fluoro, chloro, bromo and iodo, preferably chloro, bromo and iodo.

"Amino" refers to —$NH_2$.

"Cyano" refers to —CN.

"Nitro" refers to —$NO_2$.

"Benzyl" refers to —$CH_2$-phenyl.

"Carboxyl" refers to —C(O)OH.

"Carboxylate group" refers to —C(O)O(alkyl) or —C(O)O(cycloalkyl), wherein the alkyl and cycloalkyl are defined as above.

"BWL" refers to the weight loss rate (%), and when BWL is negative, it indicates that the weight of test animal is reduced.

"Substituted" means that one or more hydrogen atoms, preferably at most 5 hydrogen atoms, more preferably 1-3 hydrogen atoms, in a group, are each independently substituted by corresponding numbers of substituents. Obviously, the substituents are merely located at their possible chemical positions, and a person skilled in the art can determine the possible or impossible substitution without paying excessive efforts (through experiments or theories). For example, when an amino or hydroxyl having free hydrogen combines with the carbon atom having unsaturated (e.g., olefinic) bond, it may be unstable.

"Substitution" or "substituted" as used in this specification, unless otherwise indicated, refers to groups which may be substituted by one or more groups selected from alkyl, alkenyl, alkynyl, alkoxy, alkylthiol, alkylamino, halogen, mercapto, hydroxy, nitro, cyano, cycloalkyl, heterocyclyl, aryl, heteroaryl, cycloalkoxy, heterocycloalkoxy, cycloalkylthio, heterocycloalkylthio, amino, haloalkyl, hydroxyalkyl, carboxy, carboxylate group, —$NR^5R^6$, —C(O)$NR^5R^6$, —C(O)$R^7$, —$SO_2R^7$, —C(O)O$R^7$ or —$NR^5C(O)R^6$, wherein $R^5$ to $R^7$ are defined as in general formula (I).

"Pharmaceutical acceptable salt" refers to certain salts of the above compounds which are capable of maintaining the original biological activity and suitable for pharmaceutical use. The pharmaceutically acceptable salts of the compounds of the present invention may be metal salts, amine salts formed with suitable acids. The metal salts are preferably alkali metal, alkaline earth metal salts, suitable acids include inorganic acids and organic acids such as acetic acid, benzenesulfonic acid, benzoic acid, camphorsulfonic acid, citric acid, ethanesulfonic acid, fumaric acid, gluconic acid, glutamic acid, hydrobromic acid, hydrochloric acid, isethionic acid, lactic acid, malic acid, maleic acid, mandelic acid, methanesulfonic acid, nitric acid, phosphoric acid, succinic acid, sulfuric acid, tartaric acid, p-toluenesulfonic acid and the like. Particularly preferred acids are hydrochloric acid, hydrobromic acid, phosphoric acid and sulfuric acid, most preferably hydrochloride.

"Pharmaceutical composition" refers to comprising a mixture of one or more of the compounds described in the present invention or physiologically pharmaceutically acceptable salts or prodrugs thereof and other chemical components, and other components such as physiologically pharmaceutically acceptable carriers and excipients. The purpose of the pharmaceutical composition is to facilitate administration to an organism, which is conducive to the absorption of the active ingredient and thus displaying biologically activity.

DETAILED DESCRIPTION OF THE INVENTION

Figure 1:
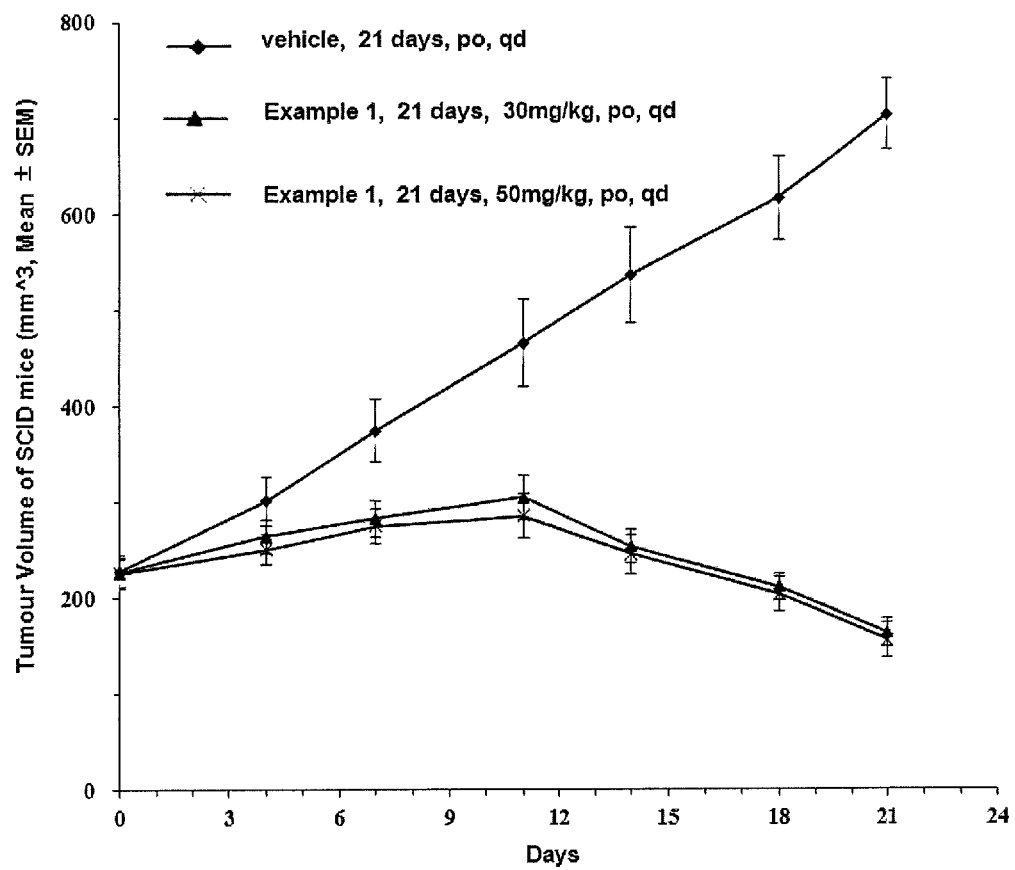
FIG. 1 is a graph showing the inhibition of tumor growth in breast cancer MCF-7 tumor-bearing mice regarding the compound in Example 1 in Test Example 4.

The invention will now be described in further detail with reference to the embodiments, and it is to be understood that these examples are not to be construed as limiting the scope of the invention.

PREPARATION EXAMPLES

The following examples illustrate the preparation of representative compounds of the present invention and related structure identification data.

$^1$H NMR spectrum was determined using a Bruker apparatus (400 MHz), and the chemical shift was expressed in ppm. Tetramethylsilane internal standard (0.00 ppm) is used. $^1$H NMR is represented as: s=singlet, d=doublet, t=triplet, m=multiplet, br=broad, dd=doublet of doublet, dt=doublet of triplet. If the coupling constant is provided, it is expressed in Hz.

Mass spectrum was determined by LC/MS instrument, and the ionization mode was ESI or APCI. MS m/z (ESI) was 100% of the measured value unless otherwise specified.

Thin layer chromatography silica gel plate used Yantai Yellow Sea HSGF254 or Qingdao GF254 silica gel plate. The dimension of the silica gel plates used in thin-layer chromatography (TLC) was 0.15 mm~0.2 mm, and the dimension of the silica gel plates used in thin layer chromatography for separation and purification products was 0.4 mm~0.5 mm.

Column chromatography used Yantai Huanghai 200 to 300 mesh silica gel as carrier.

In the following Examples, unless otherwise indicated, all temperatures are in centigrade degree, and the raw materials and reagents are commercially available or are synthesized by the known synthesis methods, the commercially available raw materials and reagents are directly used without further purification. Unless otherwise indicated, the commercial manufacturers include but not limited to Aldrich Chemical Company, ABCR GmbH&Co. KG, Acros Organics, Guangzan Chemical Technology Co., Ltd, Jing Yan Chemical Technology Co., Ltd. and Shanghai Chang Feng Biological Technology Co., Ltd. and so on.

CD$_3$OD: deuterated methanol.

CDCl$_3$: deuterated chloroform.

DMSO-d$_6$: deuterated dimethylsulfoxide.

Unless otherwise stated in the examples, the following reactions were conducted under argon atmosphere.

The argon atmosphere is provided by a reaction flask equipped with a balloon having about 1 L of argon.

In the examples, unless otherwise stated, the solution used in examples refers to an aqueous solution.

The silica gel column chromatography elution system and thin layer chromatography are applied to purify the compound, wherein the eluent system is selected from the group consisting of: A: cyclohexane and ethyl acetate system; B: dichloromethane and methanol system; C: Petroleum ether and ethyl acetate system; wherein the volume ratio of the solvents is different depending on the polarity of the compound, and a small amount of an acidic or alkaline reagent may be added for adjustment, such as acetic acid or triethylamine, and so on.

Example 1

(E)-3-(3,5-difluoro-4-((1R,3R)-2-((1-fluorocyclopropyl)methyl)-3-methyl-2,3,4,9-tetrahydro-1H-pyrido[3,4-b]indol-1-yl)phenyl)acrylic Acid -continued
Scheme 1

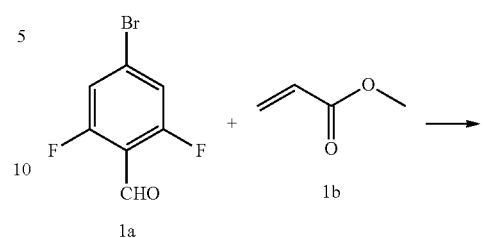

Step 1

Step 2

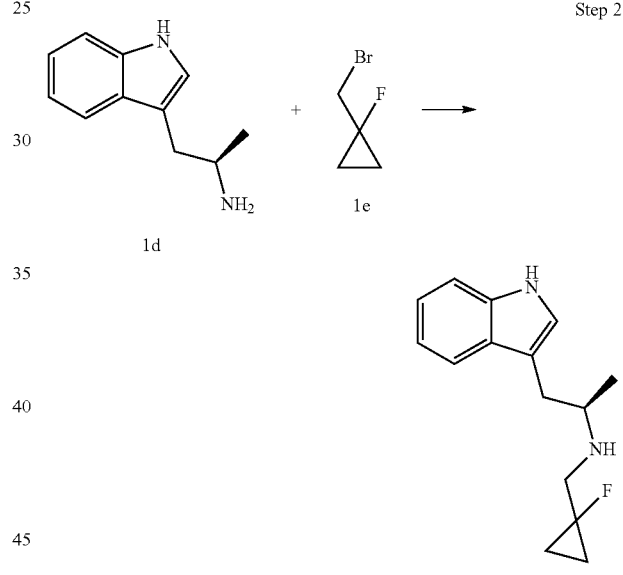

Step 3

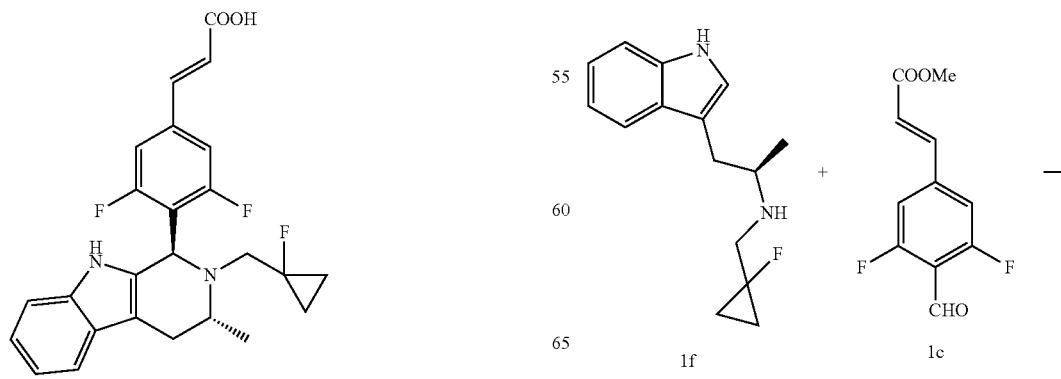

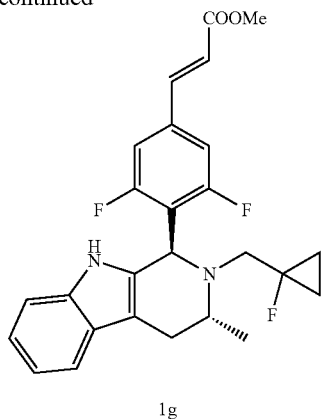

1g

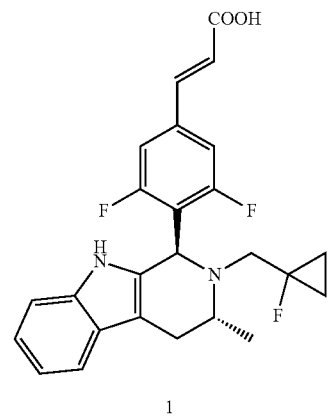

1g

Step 1

(E)-Methyl 3-(3,5-difluoro-4-formylphenyl) acrylate

4-Bromo-2,6-difluorobenzaldehyde 1a (5 g, 22.6 mmol, prepared according to a method disclosed by WO2014191726), triethylamine (6.31 ml, 45.2 mmol), palladium acetate (254 mg, 1.13 mmol) and tri-o-tolylphosphine (688 mg, 2.26 mmol) were dissolved in 100 mL dimethylformamide, and methyl acrylate 1b (2.91 mL, 33.9 mmol) was added under stirring. The reaction solution was heated to 80° C. and reacted for 5 hours. The reaction solution was cooled and the system solvent was concentrated to dryness. The reaction mixture was added with water (30 mL), and extracted with ethyl acetate (50 mL×3). The combined organic phases were washed successively with 2N hydrochloric acid (10 mL) and saturated brine (20 mL×2), dried over anhydrous sodium sulfate, filtered and concentrated under reduced pressure. The resulting residue was further separated and purified by silica gel column chromatography (eluent: cyclohexane and ethyl acetate system) to obtain (E)-methyl 3-(3,5-difluoro-4-formylphenyl)acrylate (3.73 g, yellow solid), yield: 73%.

MS m/z (ESI): 227.2 [M+1]

$^1$H NMR (400 MHz, CDCl$_3$): δ=10.34 (s, 1H), 7.57 (d, J=16.0 Hz, 1H), 7.13 (d, J=9.2 Hz, 2H), 6.52 (d, J=16.0 Hz, 1H), 3.84 (s, 3H).

Step 2

(R)—N-((1-fluorocyclopropyl)methyl)-1-(1H-indol-3-yl)propan-2-amine

Under the protection of argon gas, (R)-1-(1H-indol-3-yl)propan-2-amine 1d (1.74 g, 10 mmol, purchased from Shanghai Chang Feng Biological Technology Co., Ltd.) was dissolved in mL of dioxane, and diisopropylamine (1.51 g, 15 mmol) and 1-(bromomethyl)-1-fluorocyclopropane 1e (1.67 g, 11 mmol, purchased from Shanghai Guangzan Chemical Technology Co., Ltd.) were added therein. The reaction was carried out at 75° C. for 24 hours. The reaction solution was cooled to room temperature, quenched by the addition of a small amount of water (5 mL), dried over anhydrous sodium sulfate, filtered and the filtrate was concentrated under reduced pressure. The resulting residue was further separated and purified by silica gel column chromatography (eluent: dichloromethane and methanol system) to obtain (R)—N-((1-fluorocyclopropyl)methyl)-1-(1H-indol-3-yl)propan-2-amine 1f (0.73 g, yellow solid), yield: 30%.

MS m/z (ESI): 247.5 [M+1]

Step 3

(E)-Methyl 3-(3,5-difluoro-4-((1R,3R)-2-((1-fluorocyclopropyl)methyl)-3-methyl-2,3,4,9-tetrahydro-1H-pyrido[3,4-b]indol-1-yl)phenyl) acrylate Under the protection of argon gas, (R)—N-((1-fluorocyclopropyl)methyl)-1-(1H-indol-3-yl)propan-2-amine 1f (0.73 g, 3 mmol) was dissolved in 10 mL of toluene, and (E)-methyl 3-(3,5-difluoro-4-formylphenyl) acrylate 1c (0.678 g, 3 mmol), 20 mL of toluene and acetic acid (0.9 g, 15 mmol) were added. The reaction was carried out at 80° C. for 5 hours. The reaction solution was cooled to room temperature, quenched by the addition of a small amount of water (5 mL), dried over anhydrous sodium sulfate, filtered and the filtrate was concentrated under reduced pressure. The resulting residue was further separated and purified by silica gel column chromatography to obtain (E)-methyl 3-(3,5-difluoro-4-((1R,3R)-2-((1-fluorocyclopropyl)methyl)-3-methyl-2,3,4,9-tetrahydro-1H-pyrido[3,4-b]indol-1-yl)phenyl) acrylate 1g (0.87 g, yellow solid), yield: 60%.

MS m/z (ESI): 455.5 [M+1]

Step 4

(E)-3-(3,5-difluoro-4-((1R,3R)-2-((1-fluorocyclopropyl)methyl)-3-methyl-2,3,4,9-tetrahydro-1H-pyrido[3,4-b]indol-1-yl)phenyl)acrylic acid (E)-methyl 3-(3,5-difluoro-4-((1R,3R)-2-((1-fluorocyclopropyl)methyl)-3-methyl-2,3,4,9tetrahydro-1H-pyrido[3,4- b]indol-1-yl)phenyl) acrylate 1g (0.87 g, 1.91 mmol) was dissolved in a mixture solution of 16.5 mL tetrahydrofuran and methanol (V/V=2/1), then the mixture was added slowly into 5 mL of 7.5 M sodium hydroxide solution. The reaction was carried out at room temperature for 2 hours, and then a small amount of water was added, adjusted with 6 N hydrochloric acid until pH=3, extracted with ethyl acetate (20 mL×3). The combined organic phases were successively dried over anhydrous sodium sulfate, filtered and the filtrate was concentrated under reduced pressure. The resulting residue was further separated and purified by silica gel column chromatography (eluent: dichloromethane and methanol system) to obtain (E)-3-(3,5-difluoro-4-((1R,3R)-2-((1-fluorocyclopropyl)methyl)-3-methyl-2,3,4,9-tetrahydro-1H-pyrido[3,4-b]indol-1-yl)phenyl)acrylic acid 1 (0.76 g, yellow solid), yield: 90%.

MS m/z (ESI): 440.9 [M+1] (100%); 441.9 [M+1] (27.8%)

$^1$H NMR (400 MHz, CD$_3$OD) δ=7.61 (d, J=16.1 Hz, 1H), 7.49 (d, J=7.5 Hz, 1H), 7.34-7.21 (m, 3H), 7.13-7.00 (m, 2H), 6.59 (d, J=15.8 Hz, 1H), 5.79 (br. s., 1H), 5.50 (s, 1H), 3.95-3.84 (m, 1H), 3.56-3.43 (m, 1H), 3.14 (dd, J=4.6, 15.7 Hz, 1H), 3.07-2.94 (m, 1H), 2.79 (dd, J=6.5, 15.8 Hz, 1H), 1.32 (d, J=6.5 Hz, 3H), 1.19-1.01 (m, 2H), 0.76-0.61 (m, 2H)

Scheme 2:

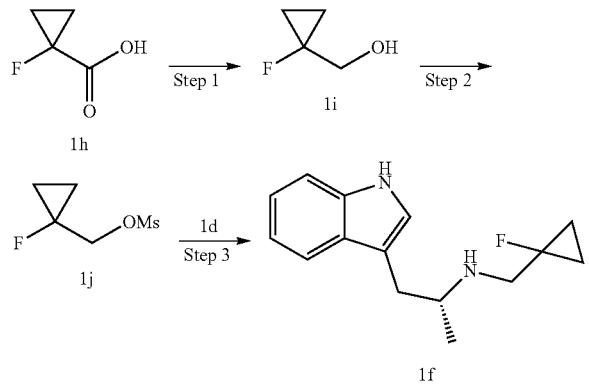

Step 1

(1-fluorocyclopropyl) Methanol

1-Fluorocyclopropanecarboxylic acid 1 h (3.12 g, 30.0 mmol) was dissolved in 75 mL ethyl ether, cooled to 0° C., and lithium aluminum hydride (1.37 g, 36.0 mmol) was added in batches. The reaction was carried out at 0° C. for 1 hour. To the reaction solution, 1.3 mL water, 1.3 mL sodium hydroxide solution (15%) and 2.6 mL water were added successively, stirred for 10 minutes, dried over anhydrous magnesium sulfate and filtered. The filter cake was washed with ethyl ether and the filtrate was concentrated under reduced pressure to obtain (1-fluorocyclopropyl) methanol ii (2.05 g, colorless liquid), yield: 76%.

$^1$H NMR (400 MHz, CDCl$_3$) δ=3.89-3.76 (m, 2H), 2.33-2.16 (m, 1H), 1.14-1.02 (m, 2H), 0.73-0.63 (m, 2H)

Step 2

(1-fluorocyclopropyl)methyl methanesulfonate (1-fluorocyclopropyl) methanol ii (1.69 g, 18.8 mmol) was dissolved in 25 mL dichloromethane, and triethylamine (3.1 mL, 22.6 mmol) was added. The reaction was protected by argon gas and cooled to −10° C., and methanesulfonyl chloride (2.26 g, 19.7 mmol) was added dropwise. Then the reaction was carried out at 0° C. for 1 hour. To the reaction solution 15 mL was added to quenched the reaction, layered, and the organic phase was washed with water (15 mL), dried over anhydrous magnesium sulfate, filtered and concentrated under reduced pressure to obtain (1-fluorocyclopropyl)methyl methanesulfonate 1j (3.02 g, colorless oil), yield: 95.5%.

$^1$H NMR (400 MHz, CDCl$_3$) δ=4.51-4.41 (m, 2H), 3.12-3.06 (m, 3H), 1.22 (td, J=7.2, 18.1 Hz, 2H), 0.86 (q, J=7.7 Hz, 2H)

Step 3

(R)—N-((1-fluorocyclopropyl)methyl)-1-(1H-indol-3-yl)propan-2-amine

Under the protection of argon gas, (1-fluorocyclopropyl) methyl methanesulfonate 1j (3.02 g, 18.0 mmol), (R)-1-(1H-indol-3-yl)propan-2-amine Id (2.84 g, 16.3 mmol) and diisopropylethylamine (5.40 mL, 32.6 mmol) were dissolved in 30 mL 1,4-dioxane. The reaction was heated to 100° C. for 5 hours. The reaction solution was cooled to room temperature and filtered by adding to the silica gel. The filter cake was washed with ethyl acetate (10 mL×2) and the filtrate was concentrated under reduced pressure. The resulting residue was further separated and purified by silica gel column chromatography (eluent: dichloromethane and methanol system) to obtain (R)—N-((1-fluorocyclopropyl) methyl)-1-(1H-indol-3-yl)propan-2-amine 1j (1.67 g, tawny solid), yield: 42%.

MS m/z (ESI): 247.5 [M+1]

The procedure of Step 1, Step 3 to Step 4 of Scheme 1 was repeated to obtain the compound of Example 1, (E)-3-(3,5-difluoro-4-((1R,3R)-2-((1-fluorocyclopropyl)methyl)-3-methyl-2,3,4,9-tetrahydro-1H-pyrido[3,4-b]indol-1-yl)phenyl)acrylic acid 1.

Examples 2-11

The synthesis method according to step 1 to step 2 in the Scheme 1 of Example 1 was repeated, except that 1-(1H-indol-3-yl)propan-2-amine Id used in the step 2 reacted with different (bromomethyl)cycloalkyl compounds, bromo substituted hydroxyalkyl compounds, (bromomethyl)aryl compounds, (bromomethyl)heteroaryl compounds or (bromomethyl)heterocyclyl compounds, and the products obtained in the step 2 were further prepared by the reaction conditions in steps 3 and 4 of Scheme 1 of Example 1 to obtain the products of Examples 2 to 11, wherein said (bromomethyl) cycloalkyl compounds were selected from (bromomethyl) cyclopropane, (bromomethyl)cyclopentane, (bromomethyl) cyclohexane, 1-(bromomethyl)-1-fluorocyclopentane, 1-(bromomethyl)-1-fluorocyclohexane, said bromo substituted hydroxyalkyl compounds were selected from 1-bromo-2-methylpropan-2-ol, said (bromomethyl)aryl compounds were selected from 1-(bromomethyl)-2-fluorobenzene and 1-(bromomethyl)-4-fluorobenzene, said (bromomethyl)heteroaryl compounds were selected from 3-(bromomethyl)pyridine, said (bromomethyl)heterocyclyl compounds were selected from 3-(bromomethyl)oxetane. The specific information was shown in Table 2 below:

TABLE 2

Structures of the compounds of Example 2-11 and confirmation data thereof.

| No. of Examples | Structure | MS | ¹H NMR |
|---|---|---|---|
| 2 | (structure) | 423.47 | ¹H NMR (400 MHz, DMSO-d$_6$): δ = 12.6 (1H, s), 10.2 (1H, s), 7.53 (1H, d), 7.41 (2H, d), 7.39 (1H, d), 7.16 (1H, d), 6.95-7.85 (2H, m), 6.69 (1H, d), 5.31 (1H, s), 3.43.-3.69 (1H, m), 2.73.-2.92 (2H, m), 2.56 (1H, dd), 2.38 (1H, dd), 1.06 (3H, d), 0.41-0.45 (1H, m) 0.08-0.25 (4H, m). |
| 3 | (structure) | 451.62 | ¹H NMR (400 MHz, DMSO-d$_6$): δ = 12.7 (1H, s), 10.1 (1H, s), 7.54 (1H, d), 7.40 (2H, d), 7.38 (1H, d), 7.17 (1H, d), 6.91-7.781 (2H, m), 6.68 (1H, d), 5.24 (1H, s), 3.44-3.65 (1H, m), 2.56-2.89 (2H, m), 2.54 (1H, dd), 2.38 (1H, dd), 1.05 (3H, d), 1.65-1.74 (1H, m) 1.35-1.60 (8H, m). |
| 4 | (structure) | 465.70 | ¹H NMR (400 MHz, DMSO-d$_6$): δ = 12.7 (1H, s), 10.3 (1H, s), 7.49 (1H, d), 7.40 (2H, d), 7.38 (1H, d), 7.15 (1H, d), 6.89-7.75 (2H, m), 6.68 (1H, d), 5.24 (1H, s), 3.44-3.65 (1H, m), 2.51-2.77 (3H, m), 2.38 (1H, dd), 1.05 (3H, d), 1.62-1.73 (1H, m) 1.27-1.60 (10H, m). |
| 5 | (structure) | 469.30 | ¹H NMR (400 MHz, DMSO-d$_6$): δ = 12.7 (1H, s), 10.1 (1H, s), 7.53 (1H, d), 7.42 (2H, d), 7.39 (1H, d), 7.15 (1H, d), 6.95-7.88 (2H, m), 6.68 (1H, d), 5.24 (1H, s), 3.42-3.64 (1H, m), 2.65-2.80 (2H, m), 2.51 (1H, dd), 2.40 (1H, dd), 1.07 (3H, d), 1.52-1.75 (4H, m) 1.43-1.57 (4H, m). |

TABLE 2-continued

Structures of the compounds of Example 2-11 and confirmation data thereof.

| No. of Examples | Structure | MS | ¹H NMR |
|---|---|---|---|
| 6 | 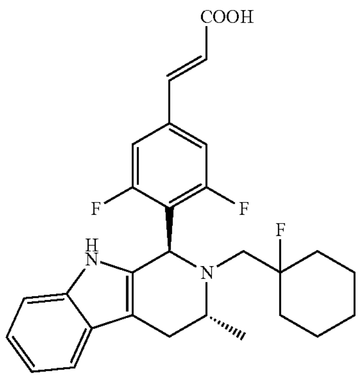 [SMILES: C[C@@H]1Cc2c([nH]c3ccccc23)[C@@H](c2c(F)cc(/C=C/C(=O)O)cc2F)N1CC1(F)CCCCC1] | 483.2 | ¹H NMR (400 MHz, DMSO-d$_6$): δ = 12.6 (1H, s), 10.3 (1H, s), 7.53 (1H, d), 7.41 (2H, d), 7.36 (1H, d), 7.15 (1H, d), 6.90-7.75 (2H, m), 6.67 (1H, d), 5.25 (1H, s), 3.41-3.64 (1H, m), 2.62-2.78 (2H, m), 2.53 (1H, dd), 2.42 (1H, dd), 1.05 (3H, d), 1.58-1.73 (4H, m) 1.39-1.62 (6H, m). |
| 7 | 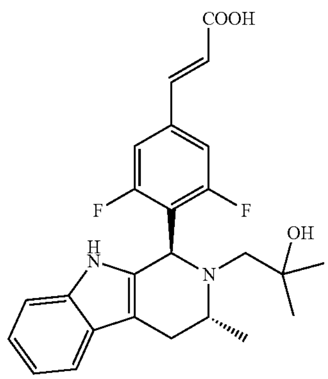 [SMILES: C[C@@H]1Cc2c([nH]c3ccccc23)[C@@H](c2c(F)cc(/C=C/C(=O)O)cc2F)N1CC(C)(C)O] | 441.48 | ¹H NMR (400 MHz, DMSO-d$_6$): δ = 12.5 (1H, s), 10.3 (1H, s), 7.55 (1H, d), 7.42 (2H, d), 7.39 (1H, d), 7.17 (1H, d), 6.97-7.90 (2H, m), 6.65 (1H, d), 5.28 (1H, s), 3.50-3.67 (1H, m), 2.8-2.92 (2H, m), 2.55 (1H, dd), 2.34 (1H, dd), 1.10 (3H, d), 1.25(3H, s), 1.23 (3H, s). |
| 8 | 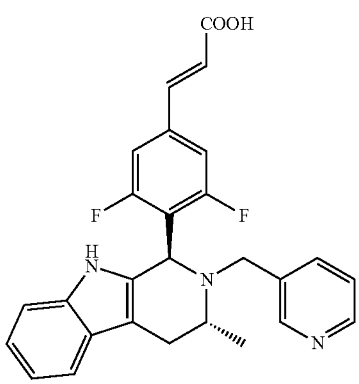 [SMILES: C[C@@H]1Cc2c([nH]c3ccccc23)[C@@H](c2c(F)cc(/C=C/C(=O)O)cc2F)N1Cc1cccnc1] | 460.52 | ¹H NMR (400 MHz, DMSO-d$_6$): δ = 12.3 (1H, s), 10.2 (1H, s), 8.59 (1H, s), 8.54 (1H, dd), 7.78-7.84 (1H, m), 7.53 (1H, d), 7.42 (2H, d), 7.37-7.43 (2H, m), 7.15 (1H, d), 6.95-7.88 (2H, m), 6.68 (1H, d), 5.31 (1H, s), 3.54-3.72 (1H, m), 3.81 (1H, d), 3.92 (1H, d), 2.57 (1H, dd), 2.36 (1H, dd), 1.05 (3H, d). |
| 9 | 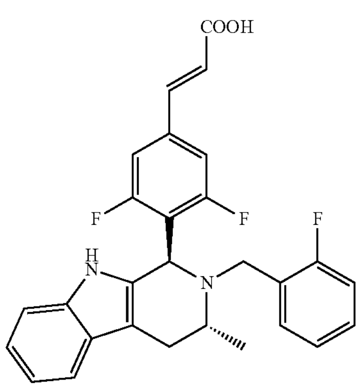 [SMILES: C[C@@H]1Cc2c([nH]c3ccccc23)[C@@H](c2c(F)cc(/C=C/C(=O)O)cc2F)N1Cc1ccccc1F] | 477.3 | ¹H NMR (400 MHz, DMSO-d$_6$): δ = 12.5 (1H, s), 10.3 (1H, s), 7.53 (1H, d), 7.42-7.56 (4H, m), 7.39 (1H, d), 7.10-7.21 (3H, m), 6.95-7.88 (2H, m), 6.68 (1H, d), 5.24 (1H, s), 3.47-3.67 (1H, m), 3.75-3.89 (2H, m), 2.58 (1H, dd), 2.35 (1H, dd), 1.05 (3H, d). |

TABLE 2-continued
Structures of the compounds of Example 2-11 and confirmation data thereof.
| No. of Examples | Structure | MS | ¹H NMR |
|---|---|---|---|
| 10 | 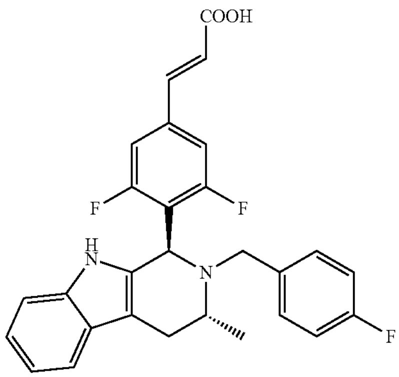 [SMILES: C[C@@H]1Cc2c([nH]c3ccccc23)[C@@H](c2c(F)cc(/C=C/C(=O)O)cc2F)N1Cc1ccc(F)cc1] | 477.5 | ¹H NMR (400 MHz, DMSO-d$_6$): δ = 12.4 (1H, s), 10.3 (1H, s), 7.53 (1H, d), 7.42 (2H, d), 7.37-7.39 (3H, m), 7.10-7.15 (3H, d), 6.95-7.83 (2H, m), 6.68 (1H, d), 5.25 (1H, s), 3.44-3.65 (1H, m), 3.69-3.84 (2H, m), 2.57 (1H, dd), 2.35 (1H, dd), 1.04 (3H, d). |
| 11 | 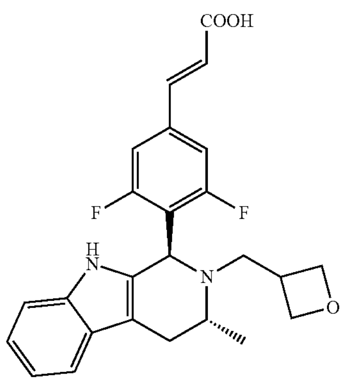 [SMILES: C[C@@H]1Cc2c([nH]c3ccccc23)[C@@H](c2c(F)cc(/C=C/C(=O)O)cc2F)N1CC1COC1] | 439.5 | ¹H NMR (400 MHz, DMSO-d$_6$): δ = 12.7 (1H, s), 10.1 (1H, s), 7.53 (1H, d), 7.42 (2H, d), 7.39 (1H, d), 7.15 (1H, d), 6.95-7.88 (2H, m), 6.68 (1H, d), 5.24 (1H, s), 4.62-4.83 (4H, m), 3.47-3.67 (1H, m), 2.91-3.01 (1H, m), 2.67-2.81 (2H, m), 2.58 (1H, dd), 2.35 (1H, dd), 1.05 (3H, d). |
Example 12
(E)-3-(3,5-difluoro-4-((1R,3R)-5-fluoro-2-(1-fluoro-cyclopropyl)methyl)-3-methyl-2,3,4,9-tetrahydro-1H-pyrido[3,4-b]indol-1-yl)phenyl)acrylic Acid
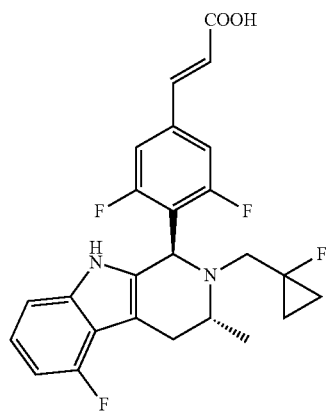
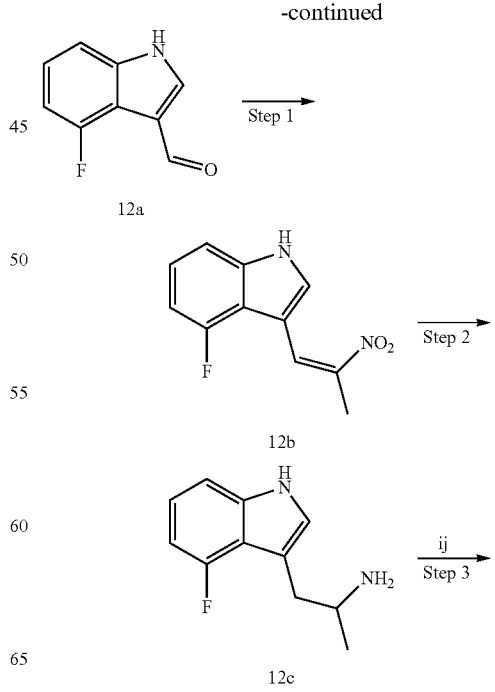

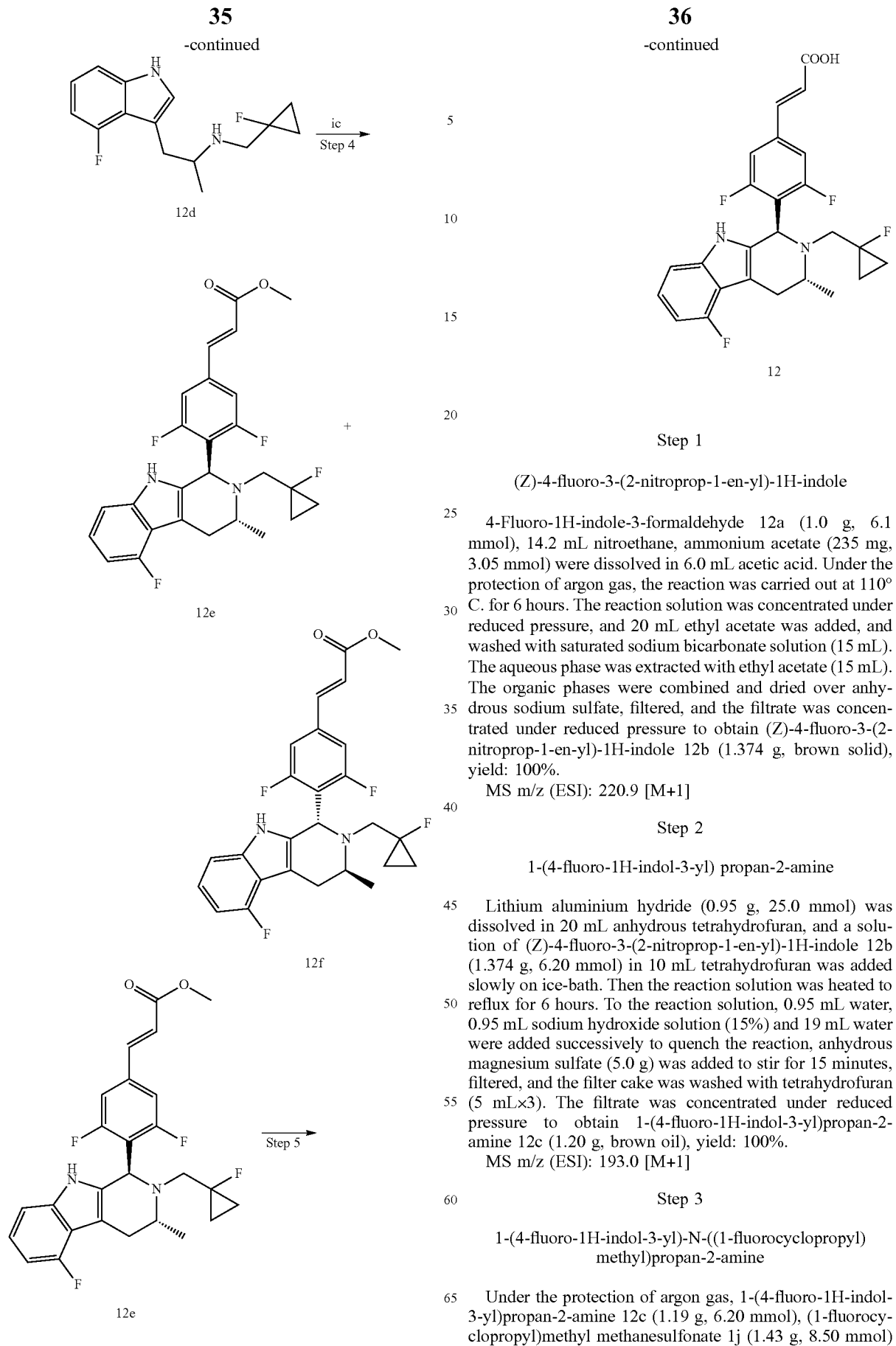

Step 1

(Z)-4-fluoro-3-(2-nitroprop-1-en-yl)-1H-indole

4-Fluoro-1H-indole-3-formaldehyde 12a (1.0 g, 6.1 mmol), 14.2 mL nitroethane, ammonium acetate (235 mg, 3.05 mmol) were dissolved in 6.0 mL acetic acid. Under the protection of argon gas, the reaction was carried out at 110° C. for 6 hours. The reaction solution was concentrated under reduced pressure, and 20 mL ethyl acetate was added, and washed with saturated sodium bicarbonate solution (15 mL). The aqueous phase was extracted with ethyl acetate (15 mL). The organic phases were combined and dried over anhydrous sodium sulfate, filtered, and the filtrate was concentrated under reduced pressure to obtain (Z)-4-fluoro-3-(2-nitroprop-1-en-yl)-1H-indole 12b (1.374 g, brown solid), yield: 100%.

MS m/z (ESI): 220.9 [M+1]

Step 2

1-(4-fluoro-1H-indol-3-yl) propan-2-amine

Lithium aluminium hydride (0.95 g, 25.0 mmol) was dissolved in 20 mL anhydrous tetrahydrofuran, and a solution of (Z)-4-fluoro-3-(2-nitroprop-1-en-yl)-1H-indole 12b (1.374 g, 6.20 mmol) in 10 mL tetrahydrofuran was added slowly on ice-bath. Then the reaction solution was heated to reflux for 6 hours. To the reaction solution, 0.95 mL water, 0.95 mL sodium hydroxide solution (15%) and 19 mL water were added successively to quench the reaction, anhydrous magnesium sulfate (5.0 g) was added to stir for 15 minutes, filtered, and the filter cake was washed with tetrahydrofuran (5 mL×3). The filtrate was concentrated under reduced pressure to obtain 1-(4-fluoro-1H-indol-3-yl)propan-2-amine 12c (1.20 g, brown oil), yield: 100%.

MS m/z (ESI): 193.0 [M+1]

Step 3

1-(4-fluoro-1H-indol-3-yl)-N-((1-fluorocyclopropyl)methyl)propan-2-amine

Under the protection of argon gas, 1-(4-fluoro-1H-indol-3-yl)propan-2-amine 12c (1.19 g, 6.20 mmol), (1-fluorocyclopropyl)methyl methanesulfonate 1j (1.43 g, 8.50 mmol)

and diisopropylethylamine (1.54 mL, 9.30 mmol) were dissolved in 12 mL 1,4-dioxane, the reaction was heated to 100° C. for 5 hours. The reaction solution was cooled to room temperature, concentrated under reduced pressure. The resulting residue was further separated and purified by silica gel column chromatography (eluent: dichloromethane: methanol system) to obtain (1-(4-fluoro-1H-indol-3-yl)-N-((1-fluorocyclopropyl)methyl)propan-2-amine 12d (975 mg, brown oil), yield: 60%.

MS m/z (ESI): 265.0 [M+1]

Step 4

(E)-Methyl 3-(3,5-difluoro-4-((1R,3R)-5-fluoro-2-((1-fluorocyclopropyl)methyl)-3-methyl-2,3,4,9-tetrahydro-1H-pyrido[3,4-]indol-1-yl)phenyl) acrylate Methyl (E)-3-(3,5-difluoro-4-((1S,3S)-5-fluoro-2-((1-fluorocyclopropyl)methyl)-3-methyl-2,3,4,9-tetrahydro-1H-pyrido[3,4-b]indol-1-yl)phenyl) acrylate Under the protection of argon gas, 1-(4-fluoro-1H-indol-3-yl)-N-((1-fluorocyclopropyl)methyl) propan-2-amine 12d (975 mg, 3.69 mmol), (E)-methyl 3-(3,5-difluoro-4-formylphenyl) acrylate 1c (848 mg, 3.69 mmol) and acetic acid (0.422 mL, 7.38 mmol) were dissolved in 10 mL toluene. The reaction was carried out at 85° C. for 7 hours. The reaction solution was cooled to room temperature, concentrated under reduced pressure. The resulting residue was further separated and purified by silica gel column chromatography (eluent: petroleum ether: ethyl acetate system). The resulting oily substance was pulped with a mixed solvent of 10 mL tetrahydrofuran and n-hexane (V/V=1/1) with a large amount of solid precipitated, filtered. The filter cake was washed with a mixed solvent of 2 mL tetrahydrofuran and n-hexane (V/V=1/1), dried to obtain (E)-methyl 3-(3,5-difluoro-4-(5-fluoro-2-((1-fluorocyclopropyl)methyl)-3-methyl-2,3,4,9-tetrahydro-1H-pyridino[3,4-b]indol-1-yl)phenyl) acrylate (322 mg, white solid), yield: 19.2%. The chiral isomers were further separated by preparative equipment and chiral column by using supercritical fluid chromatography (SFC) (chiral column: ChiralCel OJ, 250×30 mm I.D. 5 μm; mobile phase: A was CO₂, B was methanol (40%); flow rate was 60 mL/min) to obtain (E)-methyl 3-(3,5-difluoro-4-((1R,3R)-5-fluoro-2-((1-fluorocyclopropyl)methyl)-3-methyl-2,3,4,9-tetrahydro-1H-pyridino[3,4-b]indol-1-yl)phenyl) acrylate 12e (163.4 mg, white solid) and (E)-methyl 3-(3,5-difluoro-4-((1S,3S)-5-fluoro-2-((1-fluorocyclopropyl)methyl)-3-methyl-2,3,4,9-tetrahydro-1H-pyridino[3,4-b]indol-1-yl)phenyl) acrylate 12f (168.47 mg, white solid).

12e: MS m/z (ESI): 472.9 [M+1]
12f: MS m/z (ESI): 472.9 [M+1]

Step 5

(E)-3-(3,5-difluoro-4-((1R,3R)-5-fluoro-2-((1-fluorocyclopropyl)methyl)-3-methyl-2,3,4,9-tetrahydro-1H-pyrido[3,4-b]indol-1-yl)phenyl)acrylic Acid (E)-Methyl 3-(3,5-difluoro-4-((1R,3R)-5-fluoro-2-((1-fluorocyclopropyl)methyl)-3-methyl-2,3,4,9-tetrahydro-1H-pyrido[3,4-b]indol-1-yl)phenyl) acrylate 12e (163.4 mg, 0.346 mmol) was dissolved in a mixed solvent of 3 mL tetrahydrofuran and methanol (V/V=2/1), 7.5M sodium hydroxide solution (0.46 mL) was added slowly therein. The reaction was carried out at room temperature for 1 hour. The reaction solution was adjusted to pH=4 with 1 M hydrochloric acid. The solvent was eliminated by concentration under reduced pressure. 15 mL of water and 15 mL of ethyl acetate were added, layered, the aqueous phase was extracted with ethyl acetate (15 mL), and the combined organic phases were dried over anhydrous magnesium sulfate, filtered and the filtrate was concentrated under reduced pressure. The resulting residue was further separated and purified by silica gel column chromatography (eluent: petroleum ether: ethyl acetate system) to obtain (E)-3-(3,5-difluoro-4-((1R,3R)-5-fluoro-2-((1-fluorocyclopropyl)methyl)-3-methyl-2,3,4,9-tetrahydro-1H-pyrido[3,4-b]indol-1-yl)phenyl)acrylic acid 12 (54 mg, light yellow solid), yield: 34%.

MS m/z (ESI): 458.9 [M+1]
$^1$H NMR (400 MHz, CD$_3$OD) δ=7.59 (d, J=16.1 Hz, 1H), 7.25 (d, J=9.8 Hz, 2H), 7.03-6.91 (m, 2H), 6.63 (dd, J=7.7, 10.9 Hz, 1H), 6.56 (d, J=16.1 Hz, 1H), 5.45 (s, 1H), 3.76-3.66 (m, 1H), 3.26-3.14 (m, 2H), 2.89-2.70 (m, 2H), 1.20 (d, J=6.5 Hz, 3H), 0.96 (d, J=19.1 Hz, 2H), 0.62-0.52 (m, 2H)

Example 13

(E)-3-(3,5-difluoro-4-((1S,3S)-5-fluoro-2-((1-fluorocyclopropyl)methyl)-3-methyl-2,3,4,9-tetrahydro-1H-pyrido[3,4-b]indol-1-yl)phenyl)acrylic Acid

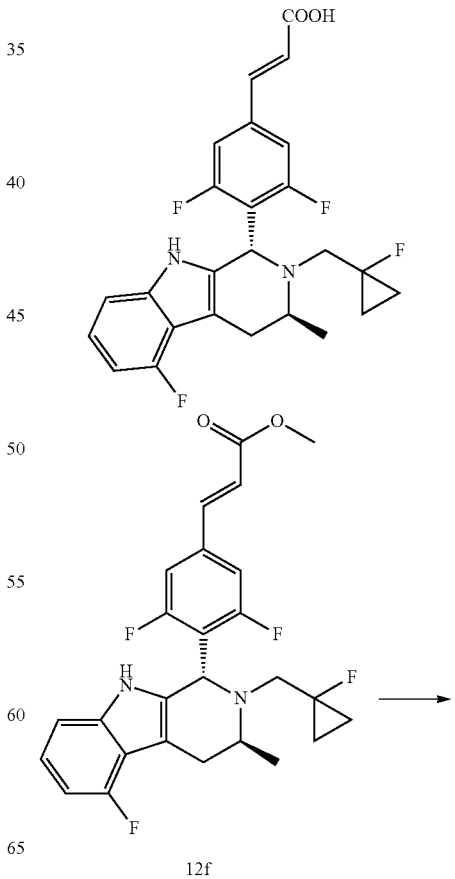

12f

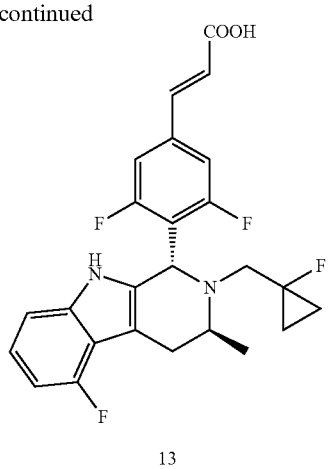

13

Step 1

(E)-3-(3,5-difluoro-4-((1S,3S)-5-fluoro-2-((1-fluoro-cyclopropyl)methyl)-3-methyl-2,3,4,9-tetrahydro-1H-pyrido[3,4-b]indol-1-yl)phenyl)acrylic Acid (E)-methyl 3-(3,5-difluoro-4-((1S,3S)-5-fluoro-2-((1-fluorocyclopropyl)methyl)-3-methyl-2,3,4,9-tetrahydro-1H-pyridino[3,4-b]indol-1-yl)phenyl) acrylate 12f (168.47 mg, 0.356 mmol) was dissolved in a mixed solvent of 3 mL tetrahydrofuran and methanol (V/V=2/1), 7.5M sodium hydroxide solution (0.475 mL) was added slowly therein. The reaction was carried out at room temperature for 1 hour. The reaction solution was adjusted to pH 4 with 1 M hydrochloric acid. The solvent was eliminated by concentration under reduced pressure. 15 mL water and 15 mL ethyl acetate were added, layered, the aqueous phase was extracted with ethyl acetate (15 mL), and the combined organic phases were dried over anhydrous magnesium sulfate, filtered and the filtrate was concentrated under reduced pressure. The resulting residue was further separated and purified by silica gel column chromatography (eluent: petroleum ether: ethyl acetate system) to obtain (E)-3-(3,5-difluoro-4-((1S,3S)-5-fluoro-2-((1-fluorocyclopropyl)methyl)-3-methyl-2,3,4,9-tetrahydro-1H-pyrido[3,4-b]indol-1-yl)phenyl)acrylic acid 13 (70 mg, light yellow solid), yield: 42.9%.

MS m/z (ESI): 458.9 [M+1]

$^1$H NMR (400 MHz, CD$_3$OD) δ=7.61 (d, J=16.1 Hz, 1H), 7.26 (d, J=10.0 Hz, 2H), 7.05-6.92 (m, 2H), 6.65 (dd, J=7.9, 10.7 Hz, 1H), 6.57 (d, J=16.1 Hz, 1H), 5.47 (s, 1H), 3.72 (d, J=5.8 Hz, 1H), 3.28-3.16 (m, 2H), 2.91-2.71 (m, 2H), 1.21 (d, J=6.5 Hz, 3H), 0.98 (d, J=18.8 Hz, 2H), 0.58 (d, J=8.5 Hz, 2H)

Biological Evaluation

Test Example 1 the Binding Assay of the Compound of the Present Invention and the Estrogen Receptor ERα

The present invention utilizes the Lantha Screen™ Time-resolved Fluorescence Resonance Energy Transfer (TR-FRET) to assess the ability of the compounds to bind to the isolated ligand domain of estrogen receptor Era in competition assay. The fluorophore (Fluormone ES2, product code P2645) and the recombinant human estrogen receptor ERα ligand binding domain (product code PV4543) using in the TR-FRET were purchased from Invitrogen. The design principle of this assay is as follows: the estrogen receptor ERα-LBD (GST) and the fluorophore-containing ligand form a receptor/fluorophore complex, followed by the addition of terbium (Tb)-labeled anti-GST antibody (product code PV3551), the indirect labeling of the receptor is achieved by the linkage with the GST on the receptor, and the ability of competitive coordination between the test compound and the fluorescent ligand with the receptor is evaluated by detecting the attenuation of the TR-FRET effect between the chromophore (Tb-anti-GST antibody) on the fluorescent label ERα and the fluorescent ligand (Fluormone ES2). We used the following sample preparation and test methods for the test of the synthesized compounds. The instrument we used is Beckman Coulter BioPAPTR FRD microfluidic workstation.

(1) Acoustic dispense 120 nL of the test compound into a black low volume 384 well assay plates;

(2) Preparation of 1×ERα-LBD/Tb-anti-GST antibody complex in ES2 buffer and incubation therein for 20 minutes;

(3) The 1×ES2 was further added to the above ERα-LBD/Tb-anti-GST antibody complex solution before the test;

(4) 12 μL of the ERα-LBD/Tb-anti-GST antibody complex solution prepared in step 3 was added to the wells of the assay plate;

(5) The plates were shielded from light and incubated at room temperature for one hour; (6) At 337 nm excitation light, the emission light at 490 nm and 520 nm was detected by BMG Phera STAR.

The test compounds of a series of concentrations (10 mM, 0.1 mM, 1 μM and 10 nM) prepared on a microplate were transferred to the analytical plate using Labcyte Echo 550. 120 nL of DMSO solution for each test compound was added to each well of the assay plate and tested at 12 different concentrations (100, 29.17, 10.42, 2.083, 1, 0.292, 0.104, 0.02083, 0.01, 0.0029, 0.00104, 0.001 μM). The TR-FRET primitive fluorescence data was used to obtain the fitting curve software such as Origin or Genedata. Half maximal inhibitory concentration IC$_{50}$ of each compound was used to characterize the competitive binding ability of the test compound with the estrogen receptor ERα. IC$_{50}$ represents the concentration of the test compound that was calculated when the coordination of the tracer fluorophore (ES2) with the estrogen receptor was reduced by 50%, and the IC$_{50}$ was determined as shown in Table 3.

Test Example 2 the Down-Regulation Assay of MCF-7 Cells on ERα

The down-regulation of the preferred compounds of the present invention on the protein level of ERα is evaluated by immunofluorescence assay using human breast cancer cell line MCF-7. MCF-7 cells used in the experiment were revived directly from frozen cells (about 5×10$^6$). The MCF-7 frozen cell line (Sigma D5921) purchased from Sigma was stored in DMEM medium containing 2 mM L-glutamic acid. 5% (v/v) Charcoal/Dextran-treated bovine serum embryonic cells were added to the revived MCF-7 cells and the cell concentration was determined using Coulter Counter.

The cells used for the test were diluted to 3.75×10$^4$ cells/mL with culture medium and 40 μL/well of the above cell suspension was transferred to 384-well black transparent bottom plates and incubated overnight at 37° C., 5%

$CO_2$. 10 mM compound stock solutions were diluted to a series of test concentrations (10 mM, 0.1 mM, 1 μM, 0.01 μM etc.) and dispensed into cell plates. 20 μL of 11.1% (v/v) aqueous formaldehyde solution (phosphate buffered saline) was added to each of the different concentrations of the test compounds and MCF-7 cell culture solution (40 μL), and the final concentration of formaldehyde in the solution was 3.7% (v/v). Cells were fixed at room temperature for 20 minutes, washed twice with 250 μL of PBS/Proclin, and then 40 μL of PBS/Proclin was added and refrigerated at 4° C. The immunostaining of the protein was performed using the automated AutoElisa kit. The PBS/Proclin solution was aspirated from each plate well and then 40 μL of PBS containing 0.5% Tween 20 (v/v) was added for cell permeation. After one hour, the plate was washed with 250 μL of PBS/0.05% Tween 20/Proclin for three times, and 20 μL of ERα rabbit monoclonal antibody (Thermofisher) in PBS/Tween™ 20/3% (w/v) BSA solution (1:1000) was added. The plates were incubated overnight at 4° C., washed three times with 250 μL of PBS/Tween™ 20/Proclin, and then 20 μL of goat anti-rabbit IgG AlexaFluor 594 or goat anti-rabbit IgG AlexaFluor 488 antibody (containing Hoechst stain (1:5000) in PBS/Tween™ 20/3% (w/v) BSA solution was added, and the system was incubated at room temperature for one hour. After the plates were washed three times with 250 μL of PBS/0.05% (v/v) Tween™ 20/Proclin, 20 μL of PBS was added and the paltes were kept in dark place at 4° C. The level of estrogen receptor ERα in MCF-7 cells was calculated through Cellomics Arrayscan detection of fluorescence emission intensity at two emission wave bands at 594 nm (24-hour time point) and 488 nm (5-hour time point). The average fluorescence emission intensity of each cell is positively correlated with the ERα receptor level of the cell. The primitive fluorescence data was used to obtain the fitting curve by software such as Origin or Genedata. Half maximal inhibitory concentration $IC_{50}$ was used to characterize the down-regulation of estrogen receptor ERα by the test compounds, which is the concentration of the test compound when the fluorescence emission intensity is reduced to 50% of the average maximum fluorescence intensity. The $IC_{50}$ is determined as shown in Table 3.

TABLE 3

Estrogen receptor ERα coordination analysis assay results and ERα down-regulation assay results

| No. of Example | $IC_{50}$ (nM) | |
|---|---|---|
| | ER Reporter | ERα down-degradation |
| 1 | A | A |
| 2 | A | A |
| 3 | B | B |
| 6 | B | B |
| 11 | B | B |
| 12 | A | A |
| 13 | C | C |

Note:
Ranges of $IC_{50}$: 0.1 nM ≤ A < 10 nM, 10 nM ≤ B < 250 nM, 250 nM ≤ C ≤ 1000 nM;

Conclusion: The compounds of the present invention are well coordinated with estrogen receptor and have a good down-regulation effect on ERα.

Test Example 3 Determination of $IC_{50}$ Values of the Compounds of the Present Invention on MCF-7 Cell 1. Reagents and Consumables Cell Counting Reagent Kit 8 (Cell Counting Kit-8, Cat# CK04-13, Dojindo);
96-well culture plate (Cat #3599, Corning Costar);
Medium and fetal bovine serum (GIBCO);
Desktop Microplate Reader (SpectraMax M5 Microplate Reader, Molecular Devices);
MCF-7 human breast cancer cell line (purchased from Shanghai cell resource center, Chinese Academy of Sciences).

2. Preparation of Reagents

Preparation of culture medium: MEM+10% FBS+0.01 mg/ml Human recombinant insulin; Preparation of the compound: The compounds were diluted with DMSO to a final concentration of 10 mM;

3. Experimental Steps (1) The logarithmic growth phase cells were collected, counted, resuspended the cells with complete culture medium. The cells were adjusted to the appropriate concentration (determined according to the cell density optimization test results) and inoculated into 96-well plates, 100 μL of cell suspension per well. The cells were incubated in an incubator for 24 hours at 37° C. with 100% relative humidity, 5% $CO_2$;

(2) The test compounds were diluted with culture medium to the corresponding concentration, and dispensed at 25 μL/well; the final concentration of the compound started from 1 μM, 4 times gradient dilution, 9 concentration points;

(3) Cells were incubated for 72 hours at 37° C. in an incubator with 100% relative humidity, 5% $CO_2$;

(4) The medium was absorbed and abandoned; the complete medium with 10% CCK-8 was added and the plates were placed in 37° C. incubator for 1 to 5 hours;

(5) The absorbance at 450 nm wavelength was measured on a SpectraMax M5 Microplate Reader after gently shaking. The inhibition rate was calculated using the absorbance at 650 nm as a reference.

4. Data Processing

The inhibition rate of the compounds on tumor cell growth was calculated by the following formula: tumor cell growth inhibition rate %=$[(A_c-A_s)/(A_c-A_b)] \times 100\%$.

$A_s$: OA of samples (cell+CCK-8+test compound);
$A_c$: OA of negative control (cell+CCK-8+DMSO);
$A_b$: OA of positive control (medium+CCK-8+DMSO).

$IC_{50}$ values of the preferable compounds on the inhibition of MCF-7 cell proliferation is conducted by Graphpad Prism 5 and using log (inhibitor) vs. response-variable slope to calculate the $IC_{50}$ values.

TABLE 4

$IC_{50}$ values of the compounds of the present invention on the inhibition of MCF-7 cell.

| No. of Example | $IC_{50}$ (nM) |
|---|---|
| 1 | 0.34 |
| 12 | 1.45 |

CONCLUSION: The compounds of the present invention have a significant inhibition effect on MCF-7 cell.

Test Example 4 the Inhibitory Effect of the Compounds of the Present Invention in SCID Mice Bearing MCF-7 Carcinoma Xenografts 1. Purpose of the Experiment This test was used to evaluate the inhibitory effect of the test compounds, which were orally administered daily for 21 days, on the growth of transplanted tumor in MCF-7 tumor-bearing SCID mice.

2. Preparation of the Test Substance

Solvent: 20% PEG400, 80% deionized water;

Preparation of the test compounds: an appropriate amount of the test compounds were weighed, dissolved in PEG400 (20%), and then 80% amount of the sterilized deionized water was added, shocked evenly. The test compounds were freshly prepared daily before administration.

3. Experimental Animals

Varieties and strains: SCID mice, SPF, female, 7 to 9 weeks old (16 to 22 grams), 100 mice, purchased from Beijing Huafu kang Biotechnology Co., Ltd., 100 mice with good health were used for the experiment, with the environment adaption time of 5 to 7 days.

4. MCF-7 Tumor Cell Culture

MCF-7 cells were cultured in RPMI1640 medium containing 10% fetal bovine serum, cultured in 37° C., 5% $CO_2$ incubator. Cells in logarithmic phase were taken before inoculating, digested with 0.25% trypsin, and then the cells were washed with PBS, resuspended in medium without serum and counted. The cell concentration was adjusted to $7.5 \times 10^7$ cells/mL (1:1 Matrigel, Extracellular Matrix Proteins, 356234, BD).

5. Animal Inoculation and Grouping

Each mouse was inoculated subcutaneously in the right axilla with 0.2 mL cell suspension ($1.5 \times 10^7$ cells/mouse) under aseptic conditions. Estrogen was administrated subcutaneously after inoculation. When the tumor grows to volume of about 150-250 mm³, the mice with similar tumor volume and good tumor shape were selected (shape to be a single spherical as much as possible, no irregular shape or multiple tumors together), 10 mice per group.

6. Animal Administration and Observation

Test compounds were administrated to each group of animals according to the weight fixed time every day as shown in table below, once a day (qd), oral administration (po) for consecutive 21 days, and the weight of animals were recorded daily.

The formation of tumor in the inoculated part of each group of animals was observed. The long diameter (Y) and the short diameter (X) of the tumor nodules were measured with a vernier caliper twice a week and calculated according to the following formula:

The volume of tumor nodules ($V$): $V=(X^2 Y)/2$.

Evaluation index of antitumor activity: tumor growth inhibition rate TGI (%), relative tumor proliferation rate T/C (%).

Tumor growth inhibition rate TGI (%): TGI (%)=($V_c$-$V_t$)/$V_c \times 100$. Where Vc is the tumor volume of the model control group and Vt is the tumor volume of the compound group.

Relative tumor volume (RTV): RTV=$V_n/V_0$. Where $V_0$ is the tumor volume just before the first time administered, and Vn is the tumor volume at the time of measurement.

Relative tumor proliferation rate: T/C (%): T/C (%)=$T_{RTV}/C_{RTV} \times 100$. Where, $T_{RTV}$ was RTV of the treatment group and $C_{RTV}$ was RTV of negative control group.

7. Results

TABLE 5

The tumor growth inhibition rate (TGI %) of the compounds of the present invention in breast cancer MCF-7 tumor bearing mice

| Groups | dosage (mg/kg) | TGI (%) | | | | | |
|---|---|---|---|---|---|---|---|
| | | Day 4 | Day 7 | Day 11 | Day 14 | Day 18 | Day 21 |
| Example 1 | 30 | 12.3 | 24.4 | 34.5 | 52.7 | 65.7 | 76.7 |
| Example 1 | 50 | 16.9 | 26.5 | 38.8 | 54.2 | 66.9 | 78.8 |
| Example 12 | 30 | 12.1 | 25.9 | 41.5 | 53.6 | 62.0 | 73.4 |
| Example 12 | 50 | 12.4 | 25.4 | 43.8 | 59.6 | 69.8 | 79.4 |

Figure 2:
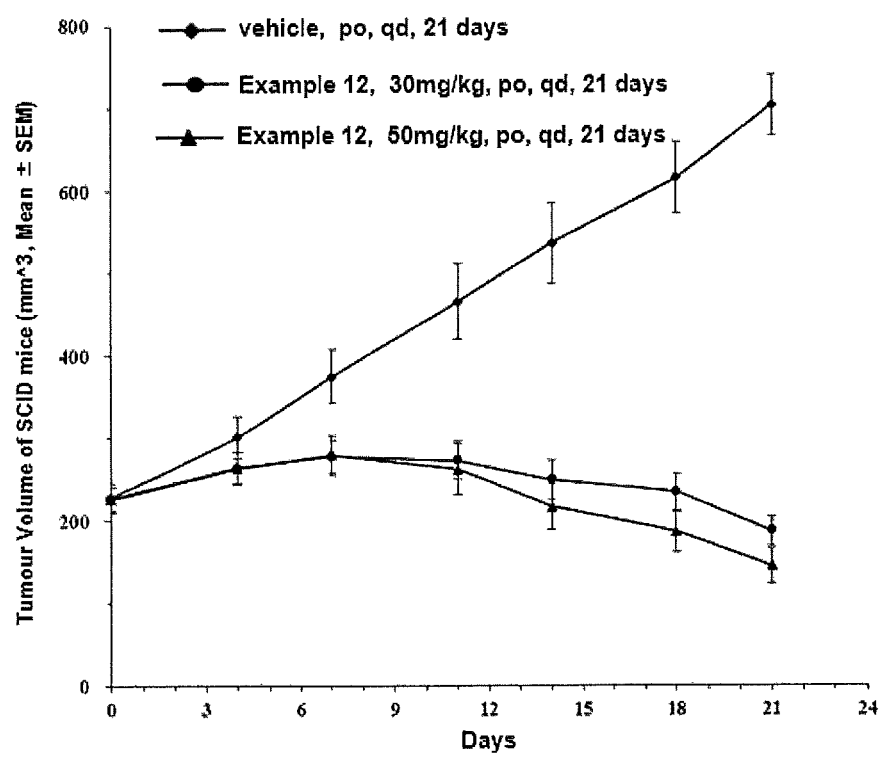
FIG. 2 is a graph showing the inhibition rate of tumor growth in breast cancer MCF-7 tumor-bearing mice regarding the compound in Example 12 in Test Example 4.
Figure 3:
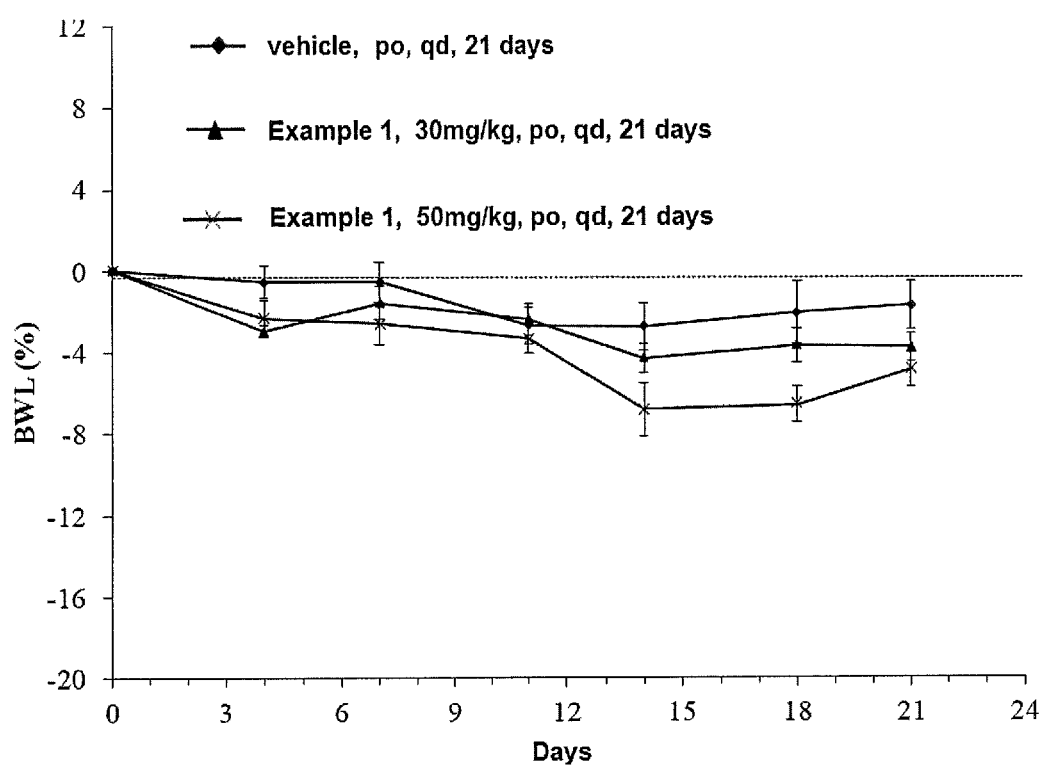
FIG. 3 is a graph showing the change in weight loss rate of breast cancer MCF-7 tumor-bearing mice regarding the compound in Example 1 of Test Example 4.
Figure 4:
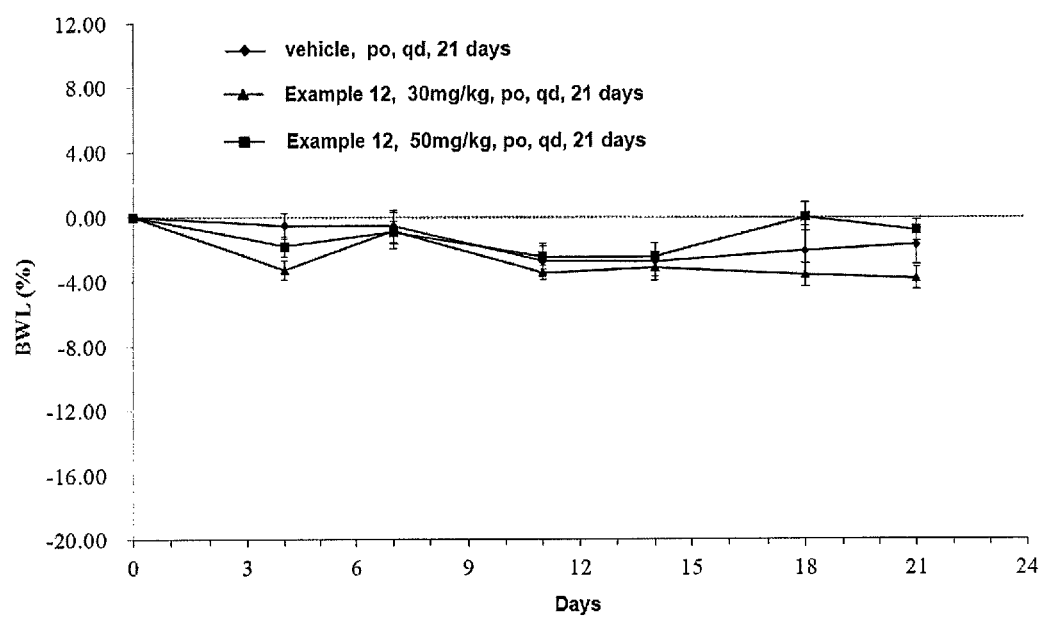
FIG. 4 is a graph showing the change in weight loss rate of breast cancer MCF-7 tumor-bearing mice regarding the compound in Example 12 in Test Example 4.

From Table 5, FIG. 1, FIG. 2, FIG. 3 and FIG. 4, it was found that the compounds of Example 1 and Example 12 of the present invention, at doses of 30 mg/kg and 50 mg/kg, have significant effect on tumor growth inhibition in human breast cancer MCF-7 bearing mice in vivo, within 21 days.

The invention claimed is:

1. A compound represented by general formula (I), or a stereoisomer, tautomer or pharmaceutically acceptable salt thereof:

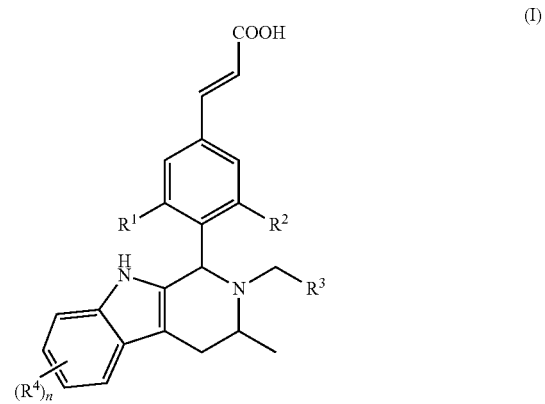

(I)

wherein:
$R^1$ and $R^2$ are each independently selected from halogen;
$R^3$ is selected from the following groups:
cycloalkyl, heterocyclyl, aryl or heteroaryl, wherein said cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —$NR^5R^6$, —$C(O)NR^5R^6$, —$C(O)R^7$, —$SO_2R^7$, —$C(O)OR^7$ or —$NR^5C(O)R^6$;
$R^4$ is each independently selected from a hydrogen atom, halogen, alkyl, alkoxy, trifluoromethyl, or cyano, wherein said alkyl or alkoxy is optionally further substituted by one or more groups selected from halogen;
$R^5$ is selected from a hydrogen atom or alkyl;
$R^6$ is selected from a hydrogen atom, alkyl, cycloalkyl, aryl or heteroaryl, wherein said alkyl, cycloalkyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

or, $R^5$ and $R^6$ together with the atoms attached to $R^5$ and $R^6$ form a 4- to 8-membered heterocyclyl, wherein said heterocyclyl is optionally further substituted by one or more groups selected from alkyl, halogen, hydroxy, cyano, nitro, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

$R^7$ is selected from a hydrogen atom, alkyl, cycloalkyl, heterocyclyl, aryl or heteroaryl, wherein said alkyl, cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

$R^8$, $R^9$ and $R^{10}$ are each independently selected from a hydrogen atom, alkyl, cycloalkyl, heterocyclyl, aryl or heteroaryl, wherein said alkyl, cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, carboxy or carboxylate group; and n is 0, 1, 2, 3 or 4.

2. The compound, or the stereoisomer, tautomer or pharmaceutically acceptable salt thereof according to claim 1, which is the compound represented by general formula (II), or a stereoisomer, a tautomer or a pharmaceutically acceptable salt thereof:

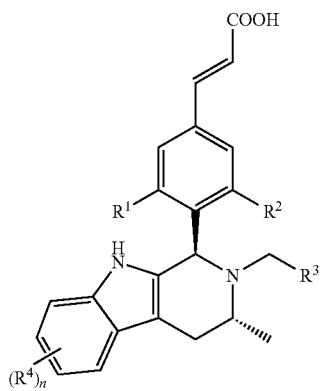

(II)

wherein, $R^1$ and $R^2$ are each independently selected from halogen;

$R^3$ is selected from the following groups:

cycloalkyl, heterocyclyl, aryl or heteroaryl, wherein said cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —$NR^5R^6$, —$C(O)NR^5R^6$, —$C(O)R^7$, —$SO_2R^7$, —$C(O)OR^7$ or —$NR^5C(O)R^6$;

$R^4$ is each independently selected from a hydrogen atom, halogen, alkyl, alkoxy, trifluoromethyl, or cyano, wherein said alkyl or alkoxy is optionally further substituted by one or more groups selected from halogen;

$R^5$ is selected from a hydrogen atom or alkyl;

$R^6$ is selected from a hydrogen atom, alkyl, cycloalkyl, aryl or heteroaryl, wherein said alkyl, cycloalkyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

or, $R^5$ and $R^6$ together with the atoms attached to $R^5$ and $R^6$ form a 4- to 8-membered heterocyclyl, wherein said heterocyclyl is optionally further substituted by one or more groups selected from alkyl, halogen, hydroxy, cyano, nitro, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

$R^7$ is selected from a hydrogen atom, alkyl, cycloalkyl, heterocyclyl, aryl or heteroaryl, wherein said alkyl, cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

$R^8$, $R^9$ and $R^{10}$ are each independently selected from a hydrogen atom, alkyl, cycloalkyl, heterocyclyl, aryl or heteroaryl, wherein said alkyl, cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, carboxy or carboxylate group; and n is 0, 1, 2, 3 or 4.

3. The compound, or the stereoisomer, tautomer or pharmaceutically acceptable salt thereof according to claim 1, wherein:

$R^3$ is selected from the following groups:

$C_3$-$C_{12}$ cycloalkyl, $C_3$-$C_{10}$ heterocyclyl, $C_6$-$C_{10}$ aryl or 5- to 10-membered heteroaryl, wherein said cycloalkyl, heterocyclyl, aryl or heteroaryl is optionally further substituted by one or more groups selected from hydroxy, halogen, halo-$C_1$-$C_{10}$ alkyl, nitro, cyano, $C_1$-$C_{10}$ alkyl, $C_1$-$C_{10}$ alkoxy, $C_3$-$C_{12}$ cycloalkyl, $C_3$-$C_{10}$ heterocyclyl, $C_6$-$C_{10}$ aryl, 5- to 10-membered heteroaryl, —$NR^5R^6$, —$C(O)NR^5R^6$, —$C(O)R^7$, —$SO_2R^7$, —$C(O)OR^7$ or —$NR^5C(O)R^6$;

$R^4$ is each independently selected from a hydrogen atom, halogen, $C_1$-$C_{10}$ alkyl, $C_1$-$C_{10}$ alkoxy, trifluoromethyl, or cyano, wherein said alkyl or alkoxy is optionally further substituted by one or more groups selected from halogen;

$R^5$ is selected from a hydrogen atom or $C_1$-$C_{10}$ alkyl;

$R^6$ is selected from a hydrogen atom, $C_1$-$C_{10}$ alkyl, $C_3$-$C_{12}$ cycloalkyl, $C_6$-$C_{10}$ aryl or 5- to 10-membered heteroaryl, wherein said alkyl, cycloalkyl, aryl or heteroaryl is optionally further substituted by one or more groups selected from hydroxy, halogen, halo-$C_1$-$C_{10}$ alkyl, nitro, cyano, $C_1$-$C_{10}$ alkyl, $C_1$-$C_{10}$ alkoxy, $C_3$-$C_{12}$ cycloalkyl, $C_3$-$C_{10}$ heterocyclyl, $C_6$-$C_{10}$ aryl, 5- to 10-membered heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

or, $R^5$ and $R^6$ together with the atoms attached to $R^5$ and $R^6$ form a 4- to 8-membered heterocyclyl, wherein said heterocyclyl is optionally further substituted by one or more groups selected from $C_1$-$C_{10}$ alkyl, halogen, hydroxy, cyano, nitro, $C_3$-$C_{12}$ cycloalkyl, $C_3$-$C_{10}$ heterocyclyl, $C_6$-$C_{10}$ aryl, 5- to 10-membered heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

$R^7$ is selected from a hydrogen atom, $C_1$-$C_{10}$ alkyl, $C_3$-$C_{12}$ cycloalkyl, $C_3$-$C_{10}$ heterocyclyl, $C_6$-$C_{10}$ aryl or 5- to 10-membered heteroaryl, wherein said alkyl, cycloalkyl, heterocyclyl, aryl or heteroaryl is optionally further substituted by one or more groups selected from hydroxy, halogen, halo-$C_1$-$C_{10}$ alkyl, nitro, cyano, $C_1$-$C_{10}$ alkyl, $C_1$-$C_{10}$ alkoxy, $C_3$-$C_{12}$ cycloalkyl, $C_3$-$C_{10}$ heterocyclyl, $C_6$-$C_{10}$ aryl, 5- to 10-membered heteroaryl, —$NR^8R^9$, —$C(O)NR^8R^9$, —$C(O)R^{10}$, —$SO_2R^{10}$, —$C(O)OR^{10}$ or —$NR^8C(O)R^9$; and $R^8$, $R^9$ and $R^{10}$ are each independently selected from a hydrogen atom, $C_1$-$C_{10}$ alkyl, $C_3$-$C_{12}$ cycloalkyl, $C_3$-$C_{10}$ heterocyclyl, $C_6$-$C_{10}$ aryl or 5- to 10-membered heteroaryl, wherein said alkyl, cycloalkyl, heterocyclyl, aryl or heteroaryl is optionally further substituted by one or more groups selected from hydroxy, halogen, halo-$C_1$-$C_{10}$ alkyl, nitro, cyano, $C_1$-$C_{10}$ alkyl, $C_1$-$C_{10}$ alkoxy, $C_3$-$C_{12}$ cycloalkyl, $C_3$-$C_{10}$ heterocyclyl, $C_6$-$C_{10}$ aryl, 5- to 10-membered heteroaryl, carboxy or carboxylate group.

4. The compound, or the stereoisomer, tautomer or pharmaceutically acceptable salt thereof according to claim 1, wherein $R^1$ and $R^2$ are F.

5. The compound, or the stereoisomer, tautomer or pharmaceutically acceptable salt thereof according to claim 1, wherein $R^4$ is each independently selected from a hydrogen atom, $C_1$-$C_3$ alkyl, halogen, alkoxy, trifluoromethyl or cyano.

6. The compound, or the stereoisomer, tautomer or pharmaceutically acceptable salt thereof according to claim 1, wherein $R^3$ is cyclopropyl, wherein said cyclopropyl is optionally further substituted by one or more groups selected from hydroxy, halogen, haloalkyl, nitro, cyano, alkyl, alkoxy, cycloalkyl, heterocyclyl, aryl, heteroaryl, —$NR^5R^6$, —$C(O)NR^5R^6$, —$C(O)R^7$, —$SO_2R^7$, —$C(O)OR^7$ or —$NR^5C(O)R^6$;

$R^5$ is selected from a hydrogen atom or alkyl;

$R^6$ is selected from a hydrogen atom, alkyl, cycloalkyl, aryl or heteroaryl, wherein said alkyl, cycloalkyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

or, $R^5$ and $R^6$ together with the atoms attached to $R^5$ and $R^6$ form a 4- to 8-membered heterocyclyl, wherein said heterocyclyl is optionally further substituted by one or more groups selected from alkyl, halogen, hydroxy, cyano, nitro, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

$R^7$ is selected from a hydrogen atom, alkyl, cycloalkyl, heterocyclyl, aryl or heteroaryl, wherein said alkyl, cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$; and $R^8$, $R^9$ and $R^{10}$ are each independently selected from a hydrogen atom, alkyl, cycloalkyl, heterocyclyl, aryl or heteroaryl, wherein said alkyl, cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, carboxy or carboxylate group.

7. The compound, or the stereoisomer, tautomer or pharmaceutically acceptable salt thereof according to claim 1, wherein $R^3$ is selected from cyclopentyl or cyclohexyl, wherein said cyclopentyl or cyclohexyl is optionally further substituted by one or more groups selected from hydroxy, halogen, haloalkyl, nitro, cyano, alkyl, alkoxy, cycloalkyl, heterocyclyl, aryl, heteroaryl, —$NR^5R^6$, —$C(O)NR^5R^6$, —$C(O)R^7$, —$SO_2R^7$, —$C(O)OR^7$ or —$NR^5C(O)R^6$;

$R^5$ is selected from a hydrogen atom or alkyl;

$R^6$ is selected from a hydrogen atom, alkyl, cycloalkyl, aryl or heteroaryl, wherein said alkyl, cycloalkyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

or, $R^5$ and $R^6$ together with the atoms attached to $R^5$ and $R^6$ form a 4- to 8-membered heterocyclyl, wherein said heterocyclyl is optionally further substituted by one or more groups selected from alkyl, halogen, hydroxy, cyano, nitro, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

$R^7$ is selected from a hydrogen atom, alkyl, cycloalkyl, heterocyclyl, aryl or heteroaryl, wherein said alkyl, cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$; and $R^8$, $R^9$ and $R^{10}$ are each independently selected from a hydrogen atom, alkyl, cycloalkyl, heterocyclyl, aryl or heteroaryl, wherein said alkyl, cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, carboxy or carboxylate group.

8. The compound, or the stereoisomer, tautomer or pharmaceutically acceptable salt thereof according to claim 1, wherein:

$R^1$ and $R^2$ are each independently selected from halogen;

$R^3$ is selected from the following groups:

cyclopropyl, cyclopentyl, cyclohexyl, $C_3$-$C_{10}$ heterocyclyl, $C_6$-$C_{10}$ aryl or 5- to 10-membered heteroaryl, wherein said cyclopropyl, cyclopentyl, cyclohexyl, $C_3$-$C_{10}$ heterocyclyl, $C_6$-$C_{10}$ aryl or 5- to 10-membered heteroaryl is optionally further substituted by one or more halogen;

$R^4$ is a hydrogen atom.

9. The compound, or the stereoisomer, tautomer or pharmaceutically acceptable salt thereof according to claim 1, wherein:

$R^1$ and $R^2$ are each independently selected from halogen;

$R^3$ is selected from cyclopropyl, cyclopentyl, cyclohexyl, $C_3$-$C_{10}$ heterocyclyl, $C_6$-$C_{10}$ aryl or 5- to 10-membered heteroaryl, wherein said cyclopropyl, cyclopentyl, cyclohexyl, $C_3$-$C_{10}$ heterocyclyl, $C_6$-$C_{10}$ aryl or 5- to 10-membered heteroaryl is optionally further substituted by one or more halogen; and $R^4$ is each independently selected from $C_1$-$C_6$ alkyl or halogen.

10. The compound, or the stereoisomer, tautomer or pharmaceutically acceptable salt thereof according to claim 9, wherein:

$R^1$ and $R^2$ are each independently halogen;

$R^3$ is cyclopropyl, wherein said cyclopropyl is further substituted by one or more halogen; and $R^4$ is each independently selected from $C_1$-$C_6$ alkyl or halogen.

11. The compound, or the stereoisomer, tautomer or pharmaceutically acceptable salt thereof according to claim 9, wherein:

$R^1$ and $R^2$ are each independently halogen;

$R^3$ is

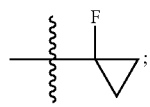 [SMILES: *C1(F)CC1]

and $R^4$ is F.

12. The compound, or the stereoisomer, tautomer or pharmaceutically acceptable salt thereof according to claim 1, wherein the compound is selected from:

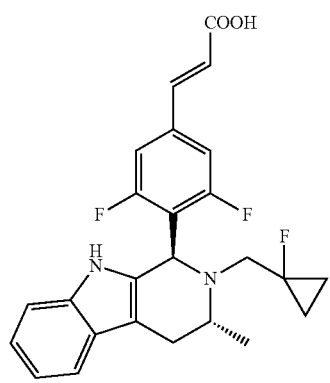

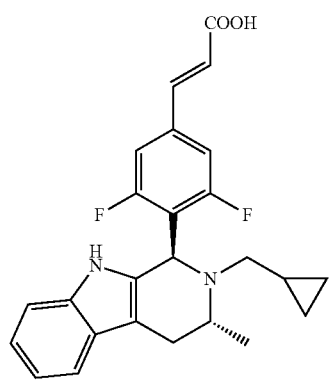

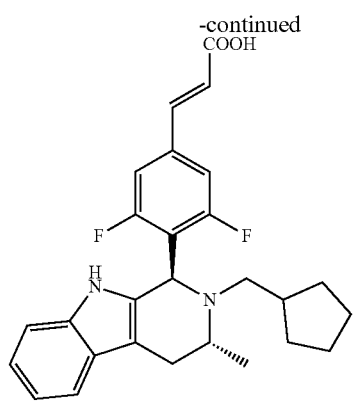

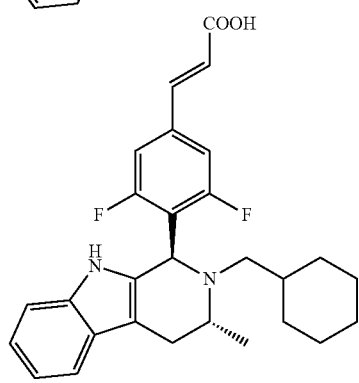

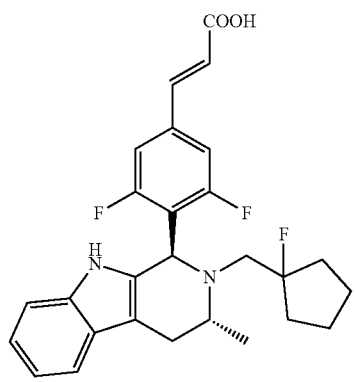

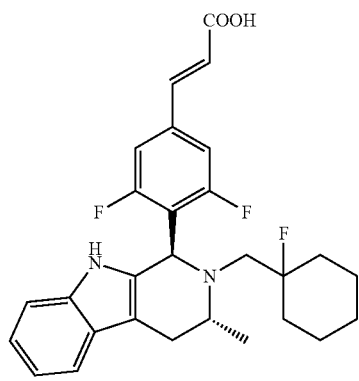

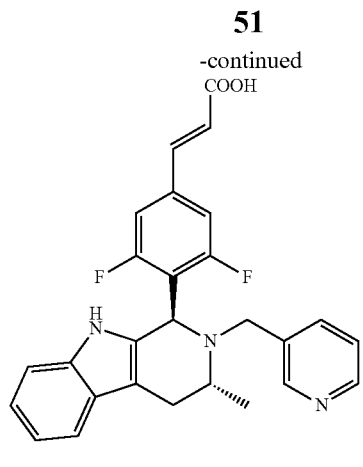
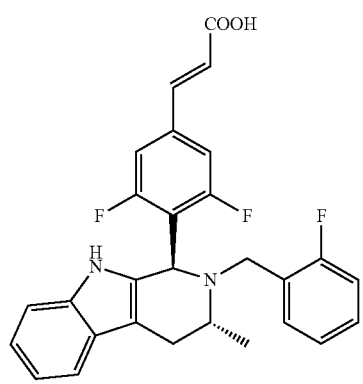
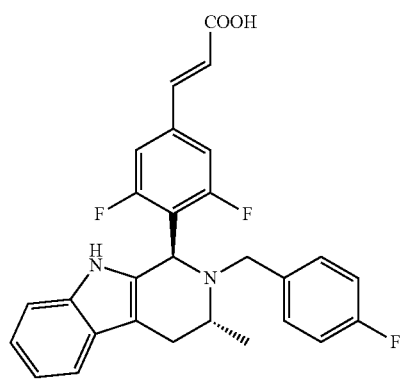
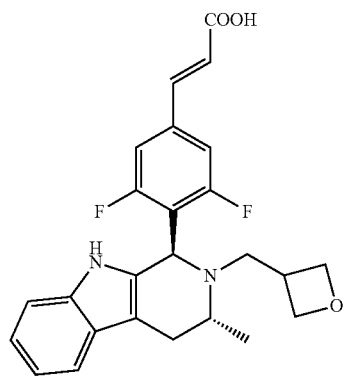
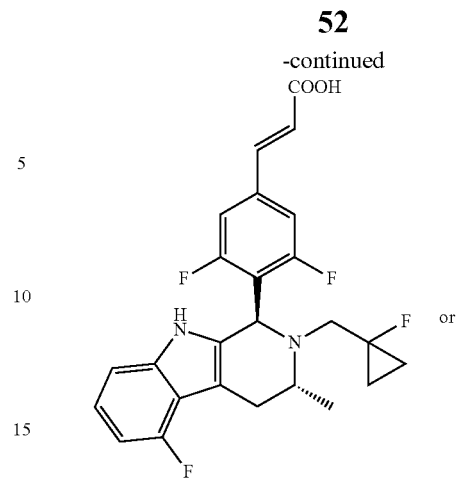
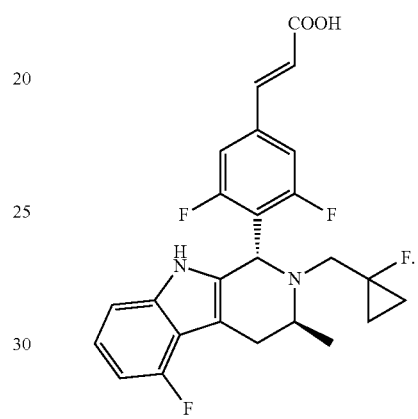
13. A process for the preparation of the compound of general formula (I) according to claim 1, comprising:
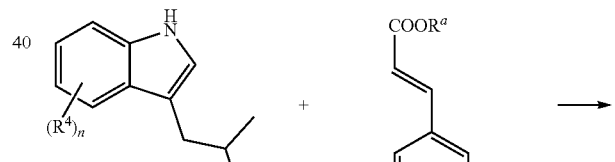
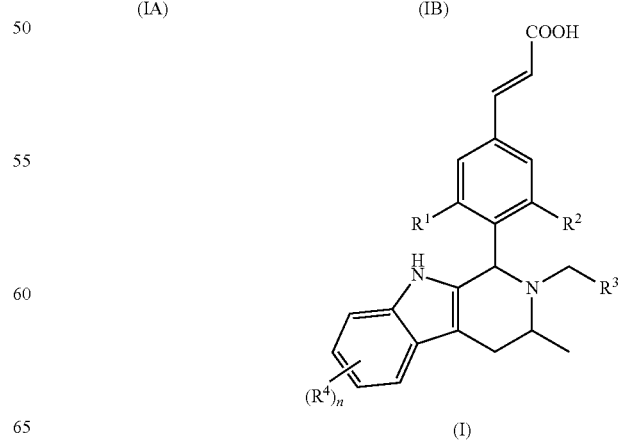

a compound of general formula (IA) is reacted with a compound of general formula (IB) under acidic condition and further ester hydrolysis to obtain the compound of general formula (I);

wherein: $R^a$ is alkyl;

$R^1$ and $R^2$ are each independently selected from halogen;

$R^3$ is selected from the following groups:

cycloalkyl, heterocyclyl, aryl or heteroaryl, wherein said cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —$NR^5R^6$, —$C(O)NR^5R^6$, —$C(O)R^7$, —$SO_2R^7$, —$C(O)OR^7$ or —$NR^5C(O)R^6$;

$R^4$ is each independently selected from a hydrogen atom, halogen, alkyl, alkoxy, trifluoromethyl, or cyano, wherein said alkyl or alkoxy is optionally further substituted by one or more groups selected from halogen;

$R^5$ is selected from a hydrogen atom or alkyl;

$R^6$ is selected from a hydrogen atom, alkyl, cycloalkyl, aryl or heteroaryl, wherein said alkyl, cycloalkyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

or, $R^5$ and $R^6$ together with the atoms attached to $R^5$ and $R^6$ form a 4- to 8-membered heterocyclyl, wherein said heterocyclyl is optionally further substituted by one or more groups selected from alkyl, halogen, hydroxy, cyano, nitro, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

$R^7$ is selected from a hydrogen atom, alkyl, cycloalkyl, heterocyclyl, aryl or heteroaryl, wherein said alkyl, cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

$R^8$, $R^9$ and $R^{10}$ are each independently selected from a hydrogen atom, alkyl, cycloalkyl, heterocyclyl, aryl or heteroaryl, wherein said alkyl, cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, carboxy or carboxylate group; and n is 0, 1, 2, 3 or 4.

14. A process for the preparation of the compound of general formula (II) according to claim 2, comprising:

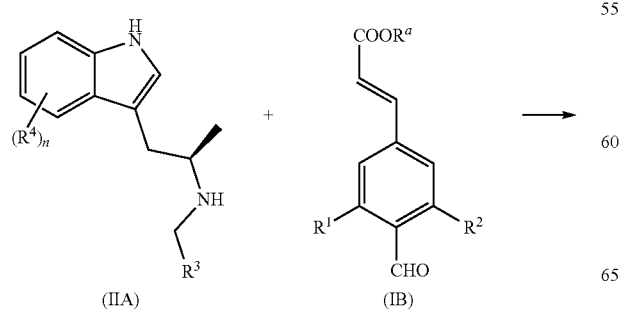
(IIA) + (IB) →

-continued

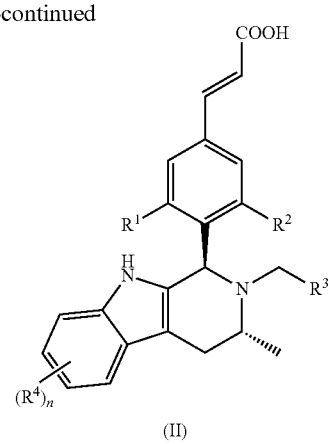
(II)

a compound of general formula (IIA) is reacted with a compound of general formula (IB) under acidic condition and further ester hydrolysis to obtain the compound of general formula (II);

wherein: $R^a$ is alkyl;

$R^1$ and $R^2$ are each independently selected from halogen;

$R^3$ is selected from the following groups:

cycloalkyl, heterocyclyl, aryl or heteroaryl, wherein said cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —$NR^5R^6$, —$C(O)NR^5R^6$, —$C(O)R^7$, —$SO_2R^7$, —$C(O)OR^7$ or —$NR^5C(O)R^6$;

$R^4$ is each independently selected from a hydrogen atom, halogen, alkyl, alkoxy, trifluoromethyl, or cyano, wherein said alkyl or alkoxy is optionally further substituted by one or more groups selected from halogen;

$R^5$ is selected from a hydrogen atom or alkyl;

$R^6$ is selected from a hydrogen atom, alkyl, cycloalkyl, aryl or heteroaryl, wherein said alkyl, cycloalkyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

or, $R^5$ and $R^6$ together with the atoms attached to $R^5$ and $R^6$ form a 4- to 8-membered heterocyclyl, wherein said heterocyclyl is optionally further substituted by one or more groups selected from alkyl, halogen, hydroxy, cyano, nitro, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

$R^7$ is selected from a hydrogen atom, alkyl, cycloalkyl, heterocyclyl, aryl or heteroaryl, wherein said alkyl, cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, —$NR^8R^9$, —$C(O)NR^8R^9$, —$C(O)R^{10}$, —$SO_2R^{10}$, —$C(O)OR^{10}$ or —$NR^8C(O)R^9$;

$R^8$, $R^9$ and $R^{10}$ are each independently selected from a hydrogen atom, alkyl, cycloalkyl, heterocyclyl, aryl or heteroaryl, wherein said alkyl, cycloalkyl, heterocyclyl, aryl or heteroaryl is optionally further substituted by one or more groups selected from hydroxy, halogen, haloalkyl, nitro, cyano, alkyl, alkoxy, cycloalkyl, heterocyclyl, aryl, heteroaryl, carboxy or carboxylate group; and n is 0, 1, 2, 3 or 4.

15. A pharmaceutical composition comprising an effective amount of the compound or the stereoisomer thereof, tautomer or pharmaceutically acceptable salt thereof according to claim 1, and a pharmaceutically acceptable carrier, excipient, or a combination thereof.

16. The pharmaceutical composition according to claim 15, further comprising an antioxidant or a metal chelating agent.

17. The compound, or the stereoisomer, tautomer or pharmaceutically acceptable salt thereof according to claim 6, wherein $R^3$ is cyclopropyl, wherein said cyclopropyl is further substituted by halogen.

18. The compound, or the stereoisomer, tautomer or pharmaceutically acceptable salt thereof according to claim 6, wherein $R^3$ is cyclopropyl, wherein said cyclopropyl is further substituted by F.

19. The compound, or the stereoisomer, tautomer or pharmaceutically acceptable salt thereof according to claim 8, wherein $R^1$ and $R^2$ are F.

20. The compound, or the stereoisomer, tautomer or pharmaceutically acceptable salt thereof according to claim 8, wherein $R^3$ is selected from cyclopropyl, cyclopentyl, cyclohexyl, $C_3$-$C_{10}$ heterocyclyl, $C_6$-$C_{10}$ aryl or 5- to 10-membered heteroaryl, wherein said cyclopropyl, cyclopentyl, cyclohexyl, $C_3$-$C_{10}$ heterocyclyl, $C_6$-$C_{10}$ aryl or 5- to 10-membered heteroaryl is optionally further substituted by one or more F.

21. The compound, or the stereoisomer, tautomer or pharmaceutically acceptable salt thereof according to claim 9, wherein $R^1$ and $R^2$ are F.

22. The compound, or the stereoisomer, tautomer or pharmaceutically acceptable salt thereof according to claim 9, wherein $R^3$ is selected from cyclopropyl, cyclopentyl, cyclohexyl, $C_3$-$C_{10}$ heterocyclyl, $C_6$-$C_{10}$ aryl or 5- to 10-membered heteroaryl, wherein said cyclopropyl, cyclopentyl, cyclohexyl, $C_3$-$C_{10}$ heterocyclyl, $C_6$-$C_{10}$ aryl or 5- to 10-membered heteroaryl is optionally further substituted by one or more halogen, wherein said halogen is F, Cl or Br.

23. The compound, or the stereoisomer, tautomer or pharmaceutically acceptable salt thereof according to claim 9, wherein $R^3$ is selected from cyclopropyl, cyclopentyl, cyclohexyl, $C_3$-$C_{10}$ heterocyclyl, $C_6$-$C_{10}$ aryl or 5- to 10-membered heteroaryl, wherein said cyclopropyl, cyclopentyl, cyclohexyl, $C_3$-$C_{10}$ heterocyclyl, $C_6$-$C_{10}$ aryl or 5- to 10-membered heteroaryl is optionally further substituted by one or more F.

24. The compound, or the stereoisomer, tautomer or pharmaceutically acceptable salt thereof according to claim 9, wherein $R^4$ is each independently selected from $C_1$-$C_6$ alkyl or halogen, wherein said halogen is F, Cl or Br.

25. The compound, or the stereoisomer, tautomer or pharmaceutically acceptable salt thereof according to claim 9, wherein $R^4$ is each independently selected from $C_1$-$C_6$ alkyl or F.

26. The compound, or the stereoisomer, tautomer or pharmaceutically acceptable salt thereof according to claim 10, wherein $R^1$ and $R^2$ are F.

27. The compound, or the stereoisomer, tautomer or pharmaceutically acceptable salt thereof according to claim 10, wherein $R^3$ is cyclopropyl, wherein said cyclopropyl is further substituted by one or more F.

28. The compound, or the stereoisomer, tautomer or pharmaceutically acceptable salt thereof according to claim 10, wherein $R^4$ is each independently selected from $C_1$-$C_6$ alkyl or F.

29. The compound, or the stereoisomer, tautomer or pharmaceutically acceptable salt thereof according to claim 11, wherein $R^1$ and $R^2$ are F.

* * * * *